(12) United States Patent
Privitera et al.

(10) Patent No.: US 10,166,010 B2
(45) Date of Patent: Jan. 1, 2019

(54) SURGICAL DEVICE FOR THE COLLECTION OF SOFT TISSUE

(71) Applicant: Devicor Medical Products, Inc., Cincinnati, OH (US)

(72) Inventors: Salvatore Privitera, West Chester, OH (US); John A. Hibner, Mason, OH (US); Jon D. Buzzard, Milford, OH (US); Michael E. Piller, Cincinnati, OH (US); David S. Iverson, Chicago, IL (US); Michael J. Reiter, Oak Park, IL (US)

(73) Assignee: Devicor Medical Products, Inc., Cincinnati, OH (US)

(*) Notice: Subject to any disclaimer, the term of this patent is extended or adjusted under 35 U.S.C. 154(b) by 755 days.

(21) Appl. No.: 14/614,776

(22) Filed: Feb. 5, 2015

(65) Prior Publication Data

US 2015/0359523 A1    Dec. 17, 2015

Related U.S. Application Data

(60) Continuation of application No. 13/873,568, filed on Apr. 30, 2013, now Pat. No. 8,979,768, which is a (Continued)

(51) Int. Cl.
*A61B 5/00* (2006.01)
*A61B 10/02* (2006.01)
(Continued)

(52) U.S. Cl.
CPC ...... *A61B 10/0275* (2013.01); *A61B 10/0266* (2013.01); *A61B 10/0283* (2013.01);
(Continued)

(58) Field of Classification Search
CPC . A61B 10/0275; A61B 19/5225; A61B 19/56; A61B 2010/0208; A61B 34/25;
(Continued)

(56) References Cited

U.S. PATENT DOCUMENTS

| | | |
|---|---|---|
| 3,732,858 A | 5/1973 | Banko |
| 3,734,099 A | 5/1973 | Bender et al. |

(Continued)

FOREIGN PATENT DOCUMENTS

| | | |
|---|---|---|
| AU | 760551 B2 | 5/2003 |
| CA | 2287087 A1 | 4/2000 |

(Continued)

OTHER PUBLICATIONS

U.S. Appl. No. 09/178,075.

(Continued)

*Primary Examiner* — May Abouelela
(74) *Attorney, Agent, or Firm* — Frost Brown Todd LLC

(57) ABSTRACT

A handheld biopsy device comprises a handpiece, a fluid collection system, and a power transmission source. The handpiece is configured for grasping by a single hand and is independently manipulatable by hand for movement of the instrument toward and away from the patient. An elongated piercer extends from the distal end of the handpiece. The piercer has a sharpened distal end and a port located proximal to the distal end for receiving a portion of tissue mass. An elongated cutter is disposed coaxially relative to a piercer lumen of the piercer. A distal blade of the cutter slides distally past the port of the piercer to sever the tissue portion drawn into the port by vacuum. The handpiece further comprises a holster for detachably connecting a cutter rotation transmission and a cutter axial transmission to the power transmission source.

24 Claims, 15 Drawing Sheets

Related U.S. Application Data continuation of application No. 11/930,701, filed on Oct. 31, 2007, now abandoned, which is a division of application No. 10/638,519, filed on Aug. 11, 2003, now Pat. No. 8,016,844, which is a continuation of application No. 09/895,732, filed on Jun. 29, 2001, now abandoned, which is a continuation of application No. 09/543,122, filed on Apr. 5, 2000, now Pat. No. 6,273,862, which is a continuation of application No. 09/178,075, filed on Oct. 23, 1998, now abandoned.

(51) Int. Cl.
A61B 34/00 (2016.01)
A61B 90/00 (2016.01)
A61B 17/00 (2006.01)

(52) U.S. Cl.
CPC .............. *A61B 34/25* (2016.02); *A61B 90/37* (2016.02); *A61B 2010/0208* (2013.01); *A61B 2017/00367* (2013.01)

(58) Field of Classification Search
CPC ..... A61B 10/02; A61B 17/3205; A61B 8/483; A61B 8/5261
USPC .................................. 600/562–568; 606/130
See application file for complete search history.

(56) References Cited

U.S. PATENT DOCUMENTS

| | | | |
|---|---|---|---|
| 3,945,375 A | 3/1976 | Banko | |
| 3,994,297 A | 11/1976 | Kopf | |
| 3,996,935 A | 12/1976 | Banko | |
| 4,052,649 A | 10/1977 | Green et al. | |
| 4,203,444 A | 5/1980 | Bonnell et al. | |
| 4,210,146 A | 7/1980 | Banko | |
| 4,246,902 A | 1/1981 | Martinez | |
| 4,250,892 A | 2/1981 | Dolhay et al. | |
| 4,316,465 A | 2/1982 | Dotson, Jr. | |
| 4,320,761 A | 3/1982 | Haddad | |
| 4,436,091 A | 3/1984 | Banko | |
| 4,517,977 A | 5/1985 | Frost | |
| 4,662,869 A | 5/1987 | Wright | |
| 4,669,154 A | 6/1987 | MacCracken | |
| 4,699,154 A | 10/1987 | Lindgren | |
| 4,705,038 A | 11/1987 | Sjostrom et al. | |
| 4,742,829 A | 5/1988 | Law et al. | |
| 4,815,462 A | 3/1989 | Clark | |
| 4,832,685 A | 5/1989 | Haines | |
| 4,844,088 A | 7/1989 | Kamblin | |
| 4,867,155 A | 9/1989 | Isaacson | |
| 4,919,146 A | 4/1990 | Rhinehart et al. | |
| 4,935,005 A | 6/1990 | Haines | |
| RE33,258 E | 7/1990 | Onik et al. | |
| 4,940,061 A | 7/1990 | Terwilliger et al. | |
| 4,943,296 A | 7/1990 | Funakubo et al. | |
| 4,944,308 A | 7/1990 | Akerfeldt | |
| 4,995,877 A | 2/1991 | Ams et al. | |
| 5,027,827 A | 7/1991 | Cody et al. | |
| 5,090,414 A | 2/1992 | Takano | |
| 5,112,299 A | 5/1992 | Pascaloff | |
| 5,133,359 A | 7/1992 | Kedem | |
| 5,133,661 A | 7/1992 | Euvard | |
| RE34,056 E | 9/1992 | Lindren et al. | |
| 5,192,292 A | 3/1993 | Cezana et al. | |
| 5,197,484 A | 3/1993 | Kornberg et al. | |
| 5,217,478 A | 6/1993 | Rexroth | |
| 5,235,261 A | 8/1993 | Philipp | |
| 5,240,011 A * | 8/1993 | Assa .................. | A61B 17/3403 600/564 |
| 5,275,609 A | 1/1994 | Pingleton et al. | |
| RE34,556 E | 3/1994 | Sjostrom et al. | |
| 5,290,303 A | 3/1994 | Pingleton et al. | |
| 5,320,635 A | 6/1994 | Smith | |
| 5,339,799 A * | 8/1994 | Kami .................. | A61B 18/14 600/109 |
| 5,353,804 A | 10/1994 | Kornberg et al. | |
| 5,403,276 A | 4/1995 | Schecter et al. | |
| 5,409,013 A | 4/1995 | Clement | |
| 5,415,169 A * | 5/1995 | Siczek ................ | A61B 6/0435 600/427 |
| 5,423,844 A | 6/1995 | Miller | |
| 5,429,138 A | 7/1995 | Jamshidi | |
| 5,433,725 A | 7/1995 | Christian et al. | |
| 5,437,630 A | 8/1995 | Daniel et al. | |
| 5,445,766 A | 8/1995 | Masumi | |
| 5,456,689 A | 10/1995 | Kresch et al. | |
| 5,469,860 A | 11/1995 | DeSantis | |
| 5,470,308 A | 11/1995 | Edwards et al. | |
| 5,487,747 A | 1/1996 | Stagmann et al. | |
| 5,490,860 A | 2/1996 | Middle et al. | |
| 5,492,130 A | 2/1996 | Chiou | |
| 5,505,210 A | 4/1996 | Clement | |
| 5,511,556 A | 4/1996 | DeSantis | |
| 5,517,990 A * | 5/1996 | Kalfas .................. | G06F 19/00 600/414 |
| 5,520,635 A | 5/1996 | Gelbfish | |
| 5,520,822 A | 5/1996 | Sun | |
| 5,526,821 A | 6/1996 | Jamshidi | |
| 5,526,822 A | 6/1996 | Burbank et al. | |
| 5,529,532 A | 6/1996 | Desrosiers | |
| 5,543,695 A | 8/1996 | Culp et al. | |
| 5,560,373 A | 10/1996 | DeSantis | |
| 5,569,284 A | 10/1996 | Young et al. | |
| 5,584,292 A * | 12/1996 | Cheung ................ | A61B 6/4233 378/37 |
| 5,601,585 A | 2/1997 | Banik et al. | |
| 5,601,601 A | 2/1997 | Tal et al. | |
| 5,602,449 A | 2/1997 | Krause et al. | |
| 5,603,724 A | 2/1997 | O'Connor | |
| 5,618,293 A | 4/1997 | Sample et al. | |
| 5,620,447 A | 4/1997 | Smith et al. | |
| 5,649,547 A | 6/1997 | Ritchart et al. | |
| 5,643,304 A | 7/1997 | Schechter et al. | |
| 5,669,876 A | 9/1997 | Schechter et al. | |
| 5,669,923 A | 9/1997 | Gordon | |
| 5,685,838 A | 11/1997 | Peters et al. | |
| 5,685,840 A | 11/1997 | Schecter et al. | |
| 5,688,974 A | 11/1997 | Devine et al. | |
| 5,689,159 A | 11/1997 | Culp et al. | |
| 5,690,660 A | 11/1997 | Devine | |
| 5,693,062 A | 12/1997 | Stegmann et al. | |
| 5,697,898 A | 12/1997 | Devine | |
| 5,769,086 A | 6/1998 | Ritchart et al. | |
| 5,772,654 A | 6/1998 | Leyva | |
| 5,775,333 A | 7/1998 | Burbank et al. | |
| 5,779,647 A | 7/1998 | Chau et al. | |
| 5,794,626 A * | 8/1998 | Kieturakis ......... | A61B 10/0266 600/567 |
| 5,795,308 A | 8/1998 | Russin | |
| 5,804,936 A | 9/1998 | Brodsky et al. | |
| 5,817,032 A | 10/1998 | Williamson, IV et al. | |
| 5,817,033 A | 10/1998 | DeSantis et al. | |
| 5,830,219 A * | 11/1998 | Bird .................... | A61B 10/0233 606/130 |
| 5,848,978 A | 12/1998 | Cecchi | |
| 5,849,023 A | 12/1998 | Mericle | |
| 5,871,454 A | 2/1999 | Majlessi | |
| 5,911,699 A | 6/1999 | Anis et al. | |
| 5,913,857 A | 6/1999 | Ritchart et al. | |
| 5,928,164 A | 7/1999 | Burbank et al. | |
| 5,928,220 A | 7/1999 | Shimoji | |
| 5,941,890 A | 8/1999 | Voegele et al. | |
| 5,944,673 A | 8/1999 | Gregoirie et al. | |
| 5,964,716 A | 10/1999 | Gregorie et al. | |
| 5,971,939 A | 10/1999 | DeSantis et al. | |
| 5,976,164 A | 11/1999 | Bencini et al. | |
| 5,980,469 A | 11/1999 | Burbank et al. | |
| 5,980,545 A | 11/1999 | Gregoire et al. | |
| 5,983,125 A * | 11/1999 | Alfano ................ | A61B 5/0075 600/473 |
| 5,984,889 A | 11/1999 | Christ et al. | |

(56) References Cited

U.S. PATENT DOCUMENTS

| | | | |
|---|---|---|---|
| 5,992,989 A | 11/1999 | Bainvel et al. | |
| 6,007,497 A | 12/1999 | Huitema | |
| 6,013,048 A | 1/2000 | Podany | |
| 6,014,581 A * | 1/2000 | Whayne | A61B 5/0422 600/523 |
| 6,017,316 A | 1/2000 | Ritchart et al. | |
| 6,019,733 A | 2/2000 | Farascioni | |
| 6,022,324 A | 2/2000 | Skinner | |
| 6,022,362 A | 2/2000 | Lee et al. | |
| 6,050,955 A | 4/2000 | Bryan et al. | |
| 6,077,230 A | 6/2000 | Gregorie et al. | |
| 6,077,497 A | 6/2000 | Park et al. | |
| 6,080,113 A | 6/2000 | Heneveld et al. | |
| 6,086,544 A | 7/2000 | Hibner et al. | |
| 6,096,042 A | 8/2000 | Herbert | |
| 6,108,439 A * | 8/2000 | Ishiguro | A61B 8/12 382/131 |
| 6,109,270 A * | 8/2000 | Mah | A61B 5/7264 128/924 |
| 6,120,462 A | 9/2000 | Hibner et al. | |
| 6,142,955 A | 11/2000 | Farascioni et al. | |
| 6,162,187 A | 12/2000 | Buzzard et al. | |
| 6,174,291 B1 * | 1/2001 | McMahon | A61B 5/0071 600/564 |
| 6,238,355 B1 | 5/2001 | Daum | |
| 6,245,084 B1 | 6/2001 | Mark et al. | |
| 6,261,302 B1 | 7/2001 | Voegele et al. | |
| 6,273,862 B1 | 8/2001 | Privitera et al. | |
| 6,346,107 B1 | 2/2002 | Cucin | |
| 6,432,065 B1 * | 8/2002 | Burdorff | A61B 10/0275 600/566 |
| 6,594,518 B1 * | 7/2003 | Benaron | A61B 5/0059 600/342 |
| 8,016,844 B2 | 9/2011 | Privitera et al. | |
| 8,206,409 B2 | 6/2012 | Privitera et al. | |
| 8,979,768 B2 | 3/2015 | Privitera et al. | |
| 2001/0047183 A1 | 11/2001 | Privitera et al. | |
| 2005/0177117 A1 | 8/2005 | Crocker et al. | |
| 2008/0146965 A1 | 6/2008 | Privitera et al. | |
| 2009/0198149 A1 | 8/2009 | Privitera et al. | |
| 2012/0215129 A1 | 8/2012 | Privitera et al. | |
| 2013/0237878 A1 | 9/2013 | Privitera et al. | |

FOREIGN PATENT DOCUMENTS

| | | |
|---|---|---|
| CH | 173651 | 12/1934 |
| DE | 19651132 A1 | 6/1998 |
| EP | 0 378 692 | 7/1990 |
| EP | 0 479 261 | 4/1992 |
| EP | 0 497 520 | 8/1992 |
| EP | 0 541 377 | 7/1995 |
| EP | 0 807 412 | 11/1997 |
| EP | 0 995 400 A1 | 4/2000 |
| EP | 1 745 746 A1 | 1/2007 |
| FR | 2685619 | 7/1993 |
| GB | 2018601 | 10/1979 |
| GB | 2174219 | 10/1986 |
| JP | 4364364 B2 | 11/2009 |
| WO | WO 1993/014707 | 8/1993 |
| WO | WO 1995/000718 | 1/1995 |
| WO | WO 1995/025465 | 9/1995 |
| WO | WO 1995/027443 | 10/1995 |
| WO | WO 1997/020504 | 6/1997 |
| WO | WO 1997/024991 | 7/1997 |
| WO | WO 1997/029594 | 8/1997 |
| WO | WO 1998/006338 | 2/1998 |
| WO | WO 1998/008446 | 3/1998 |
| WO | WO 1998/009561 | 3/1998 |
| WO | WO 1998/020763 | 5/1998 |
| WO | WO 1998/044160 | 10/1998 |
| WO | WO 1998/048344 | 10/1998 |
| WO | WO 1998/051220 | 11/1998 |
| WO | WO 1999/018296 | 4/1999 |
| WO | WO 2003/010311 | 2/2003 |

OTHER PUBLICATIONS

U.S. Appl. No. 09/895,732.
U.S. Appl. No. 11/930,701.
U.S. Appl. No. 12/372,998.
U.S. Appl. No. 13/462,030.
U.S. Appl. No. 13/868,245.
Burbank, F., "Stereotactic Breast Biopsy of Atypical Ductal Hyperplasia and Ductal Carcinoma in Situ Lesions: Improved Accuracy with Directional, Vacuum-Assisted Biopsy," Radiology, vol. 202 (1997) pp. 843-847.
Burbank, F., "Stereotactic Breast Biopsy: Its History, Its Present, and Its Future," The American Surgeon, vol. 62 (1996) pp. 128-150.
Mammotone Biopsy System User Guide for the Fischer Imaging Stereotactic Prone Table, Biopsys Medical, Inc. (1997) pp. 1-209.
Mammotone Biopsy System User Guide for the Lorad Stereotactic Prone Table, Biopsys Medical, Inc. (1997) pp. 1-23.
Mammotone Multi-Probe and Power Driver Instruction for Use, Biopsys Medical, Inc. (1997) p. 1-3.
Parker, S.H. et al., "A Practical Approach to Minimally Invasive Breast Biopsy," Radiology, vol. 200 (196) pp. 11-20.
Parker, S.H. et al., "Critical Pathways in Percutaneous Breast Intervention," Radio Graphics, vol. 15(4) (1995) pp. 946-950.
Parker, S.H., "Evolution of the Standard Stereotactic Biopsy Technique," 27th National Conference on Breast Cancer (1996) pp. 114-115.
Parker, S.H. et al., "Performing a Breast Biopsy with a Directional, Vacuum-assisted Biopsy Instrument," Radio Graphics, vol. 17(5) (1997) pp. 1233-1252.
European Search Report dated Feb. 3, 2000 for Application No. EP 99308348.4, 3 pgs.
European Communication dated Aug. 21, 2003 for Application No. EP 99308348.4, 5 pgs.
European Communicated dated May 17, 2004 for Application No. EP 99308348.4, 3 pgs.
European Search Report and Written Opinion dated Dec. 19, 2006 for Application No. EP 06076965.0, 6 pgs.
European Communication dated Nov. 18, 2008 for Application No. EP 06076965.0, 3 pgs.
European Communication dated Jan. 20, 2011 for Application No. EP 06076965.0, 4 pgs.
International Search Report dated Apr. 4, 2003 for Application No. PCT/US2002/016696.
U.S. Appl. No. US 09/178,075, filed Oct. 23, 1998.

* cited by examiner

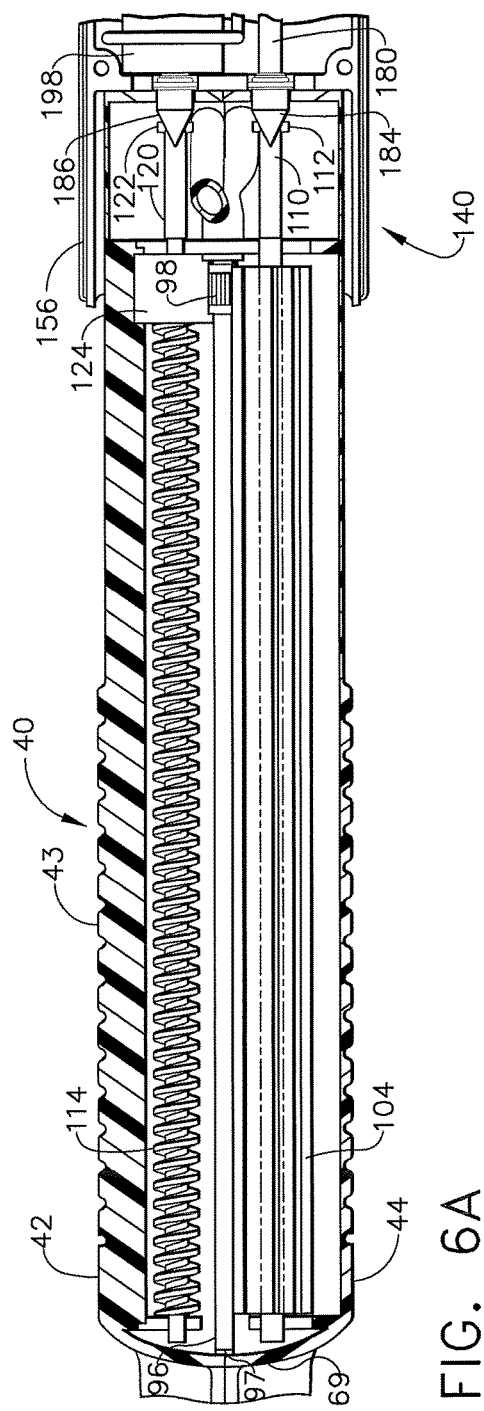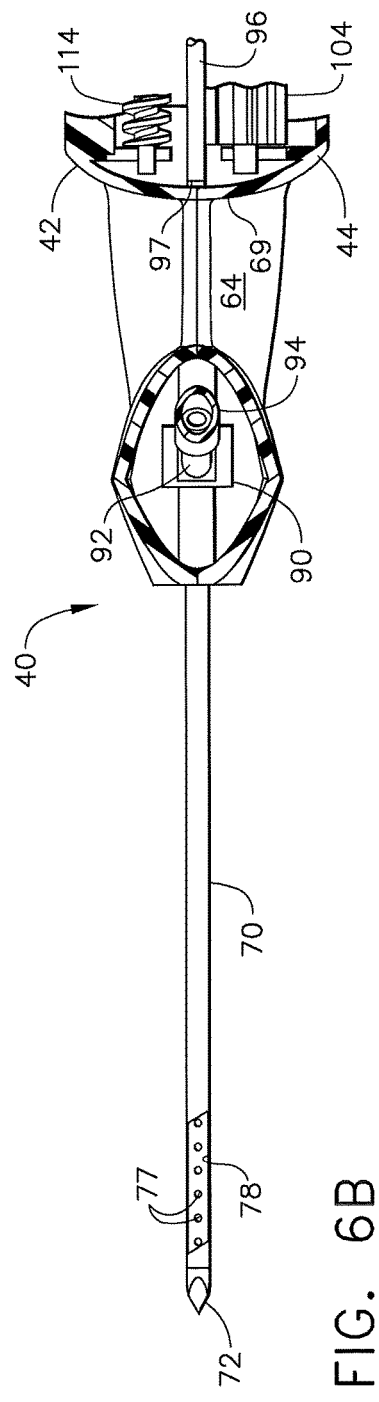
FIG. 6A
FIG. 6B

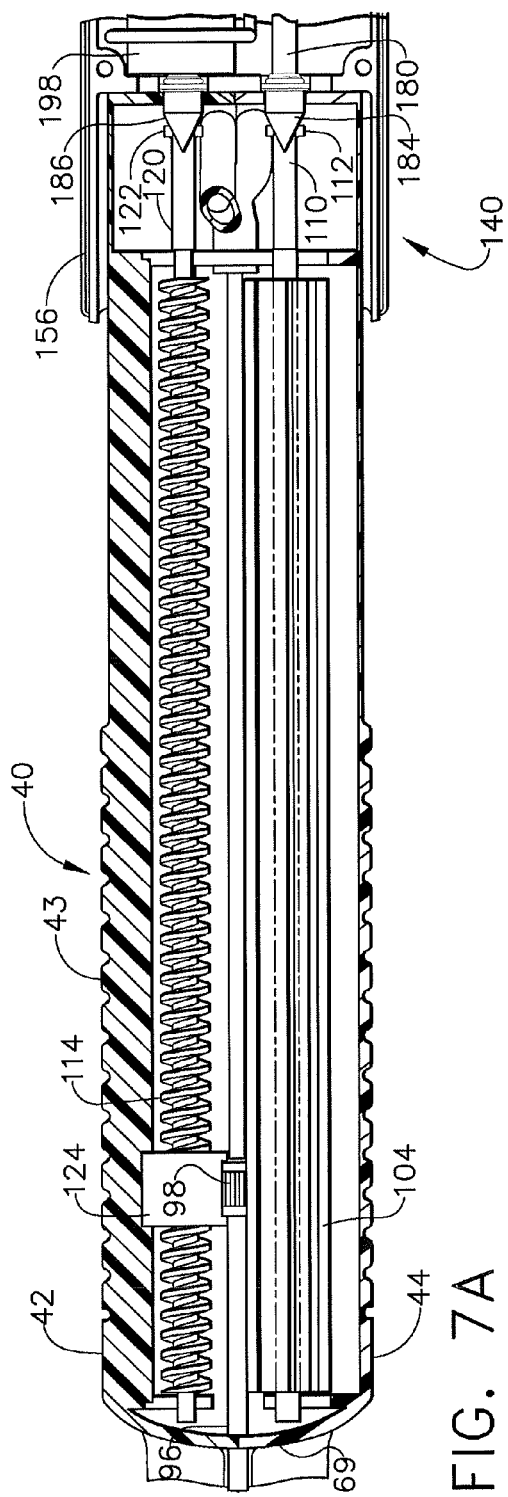
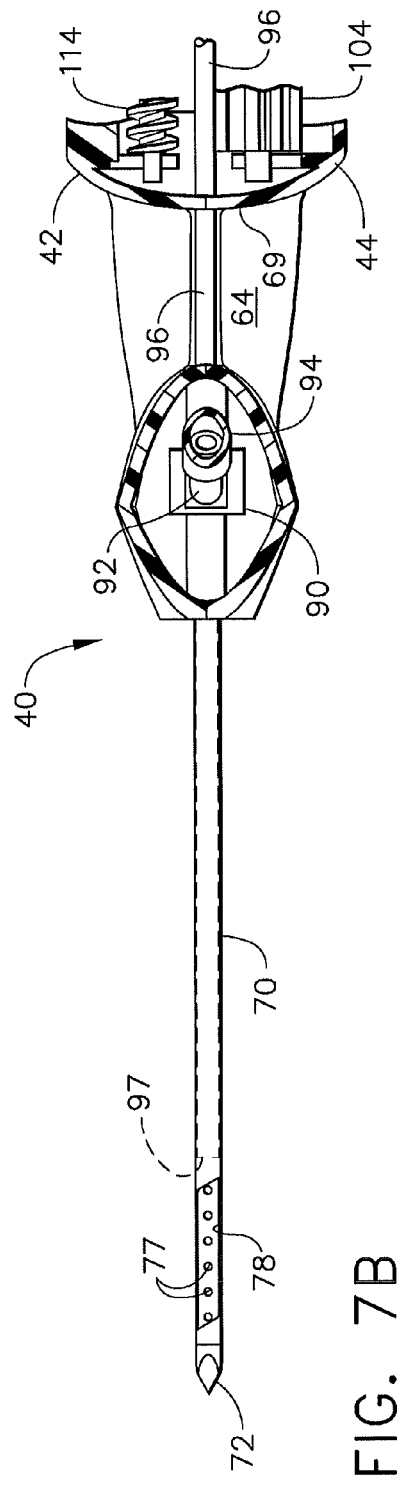
FIG. 7A
FIG. 7B

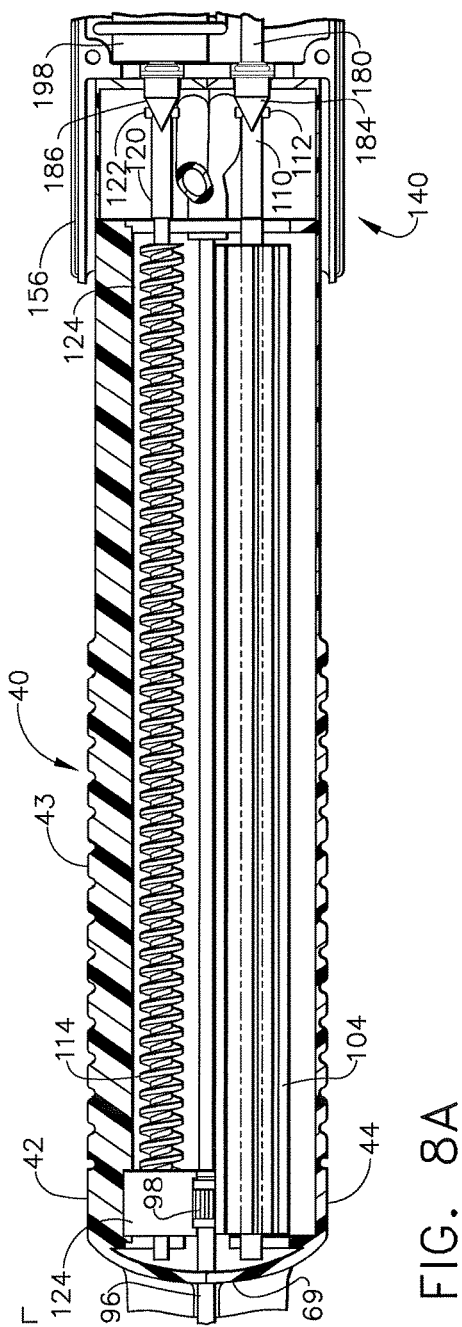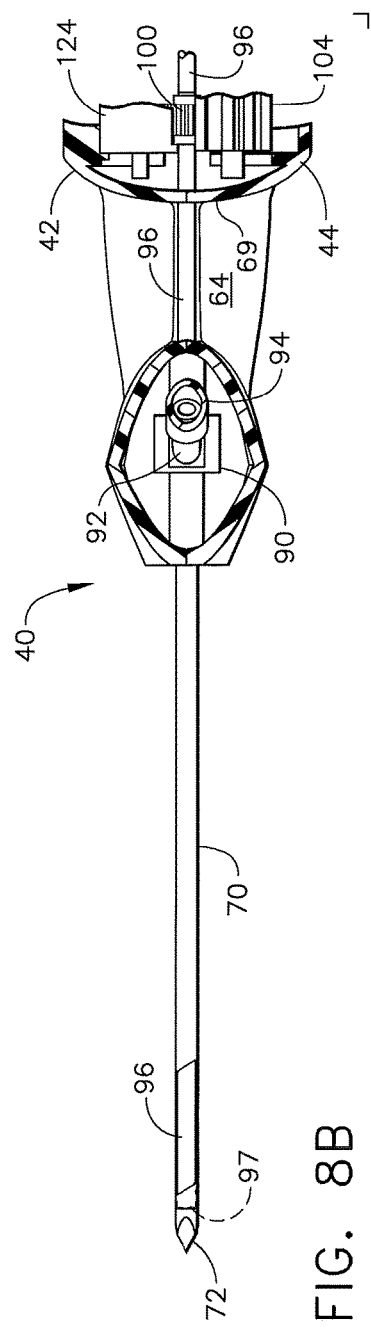
FIG. 8A
FIG. 8B

SURGICAL DEVICE FOR THE COLLECTION OF SOFT TISSUE

RELATED PATENTS AND PATENT APPLICATIONS

This application is a continuation of U.S. patent application Ser. No. 13/873,568, filed Apr. 30, 2013, which is a continuation of U.S. patent application Ser. No. 11/930,701, filed Oct. 31, 2007, which is a divisional of U.S. patent application Ser. No. 10/638,519, filed Aug. 11, 2003, issued as U.S. Pat. No. 8,016,844 on Sep. 13, 2011, which is a continuation of U.S. patent application Ser. No. 09/895,732, filed Jun. 29, 2001, which is a continuation of U.S. patent application Ser. No. 09/543,122, filed Apr. 5, 2000, issued as U.S. Pat. No. 6,273,862, which is a continuation of U.S. patent application Ser. No. 09/178,075, filed Oct. 23, 1998.

Subject matter of this application is related to the following U.S. patent application Ser. No. 08/825,899 filed on Apr. 2, 1997, now abandoned; Ser. No. 09/107,845 filed on Jun. 30, 1998, issued as U.S. Pat. No. 6,007,497 on Dec. 28, 1999. Subject matter of this application is further related to the following U.S. patent application Ser. No. 09/282,142, filed Mar. 31, 1999, issued as U.S. Pat. No. 6,086,544; Ser. No. 09/282,140, filed Mar. 31, 1999, issued as U.S. Pat. No. 6,120,462 on Sep. 19, 2000.

FIELD OF THE INVENTION

The present invention relates, in general, to devices for tissue sampling and, more particularly, to improved biopsy probes for acquiring subcutaneous biopsies and for removing lesions.

BACKGROUND OF THE INVENTION

The diagnosis and treatment of patients with cancerous tumors, pre-malignant conditions, and other disorders has long been an area of intense investigation. Non-invasive methods for examining tissue include palpation, X-ray, MRI, CT, and ultrasound imaging. When the physician suspects that a tissue may contain cancerous cells, a biopsy may be done using either an open procedure or a percutaneous procedure. For an open procedure, a scalpel is used by the surgeon to create a large incision in the tissue in order to provide direct viewing and access to the tissue mass of interest. The entire mass (excisional biopsy) or a part of the mass (incisional biopsy) may then be removed. For a percutaneous biopsy, a needle-like instrument is used through a very small incision to access the tissue mass of interest and to obtain a tissue sample for later examination and analysis. The advantages of the percutaneous method as compared to the open method may be significant and may include: less recovery time for the patient, less pain, less surgical time, lower cost, and less disfigurement of the patient's anatomy. Use of the percutaneous method in combination with imaging devices such as X-ray and ultrasound has resulted in highly reliable diagnoses and treatments.

Generally there are two ways to obtain percutaneously a portion of tissue from within the body, by aspiration or by core sampling. Aspiration of the tissue through a fine needle requires the tissue to be fragmented into pieces small enough to be withdrawn in a fluid medium. The method is less intrusive than other known sampling techniques, but one can only examine cells in the liquid (cytology) and not the cells and the structure (pathology). In core biopsy, a core or fragment of tissue is obtained for histologic examination which may be done via a frozen or paraffin section.

The type of biopsy used depends mainly on various factors present in the patient, and no single procedure is ideal for all cases. Core biopsy, however, is very useful in a number of conditions and is widely used by physicians.

A number of biopsy devices have been designed and commercialized for use in combination with imaging devices. One such biopsy instrument is the BIOPTY gun, available from C.R. Bard, Inc. and described in U.S. Pat. Nos. 4,699,154 and 4,944,308 as well as in U.S. Reissued Pat. No. Re. 34,056. The BIOPTY gun is a core sampling biopsy device in which the biopsy needle is spring-powered. However, when using the BIOPTY gun, the breast or organ must be punctured and the device is re-inserted each time a sample is taken. Another core biopsy device is the TRUE CUT needle manufactured by Travenol Laboratories. This TRUECUT needle collects a single core of tissue using a pointed element with a side-facing notch to receive tissue and an outer, sharpened sliding cannula to cut the core sample from the surrounding tissue.

Aspiration biopsy devices for obtaining biopsy samples from the body are described in the following: U.S. Pat. No. 5,492,130; U.S. Pat. No. 5,526,821; U.S. Pat. No. 5,429,138; and U.S. Pat. No. 5,027,827. These patents describe devices which use the aspiration method of liquid suspended tissue extraction rather than core sampling to extract tissue.

To overcome operator error associated with such devices, and to enable multiple sampling of the tissue without having to reenter the tissue for each sample, a biopsy instrument now marketed under the tradename MAMMOTOME was developed. Embodiments of the invention are described in U.S. Pat. No. 5,526,822. The MAMMOTOME instrument is a type of image-guided, percutaneous, coring, breast biopsy instrument. It is vacuum-assisted and some of the steps for retrieving the tissue samples have been automated. The physician uses this device to capture "actively" (using the vacuum) the tissue prior to severing it from the body. This allows for sampling tissues of varying hardness. In the MAMMOTOME biopsy instrument, the cutter is rotated using a motor drive mounted in the instrument while the surgeon manually moves the cutter back and forth by a knob on the outside of the instrument. Thus, the surgeon is able, through tactile feedback, to determine whether the blade is effectively cutting tissue or if there is a problem, such as binding or stalling. The surgeon may then adjust the speed at which the blade is moved through the tissue, stop the blade, or back the blade away from the tissue. The device can also be used to collect multiple samples in numerous positions about its longitudinal axis, without removing the biopsy needle from the body. These features allow for substantial sampling of large lesions and complete removal of small ones. In the MAMMOTOME, a vacuum chamber is attached alongside and fluidly connected to an elongated, hollow piercer. The vacuum supplied through the vacuum chamber pulls tissue into the lateral receiving port of the hollow piercer.

For breast biopsies, the devices described so far are most commonly used in combination with either X-ray or ultrasound imaging to locate suspicious tissue, although other imaging modalities such as magnetic resonance imaging are also available. When using, for example, the MAMMOTOME biopsy device with an X-ray stereotactic table, the biopsy device is attached to a movable, mechanical mounting arm. The patient lies face down on the table and the patient's breast is guided through an opening in the stereotactic table. Several X-ray images of the breast are taken from different angles to determine the location of the calcifications, lesions, etc. which are to be removed from the breast. Next the mounting arm is manually repositioned so that the biopsy device is properly aligned with the breast. Then the mounting arm is manipulated to push piercer of the biopsy device into the breast until the tip of the piercer is positioned alongside the tissue to be sampled. Additional X-ray images are then made to confirm that the port on the distal end of the piercer is in the proper position to collect the desired tissue portions. The biopsy device is then used to retrieve one or more core samples of tissue. Additional X-ray images are taken to confirm the removal of the suspect tissue. Sometimes the biopsy device and mounting arm must be repositioned during the procedure so that the tip of the piercing element is in a new location in order to retrieve more tissue samples. As this brief description illustrates, there are many time consuming steps in getting the biopsy device properly positioned to retrieve the desired tissue. In addition, the accessibility of certain parts of the breast may be hindered by the degrees of freedom of the movement of the mounting arm. Also, the size of the stereotactic table and associated equipment precludes portability of the system. It is not possible, for example, to have a number of patients being prepared for the procedure in separate rooms of a clinic, if there is only one room set-up for doing the procedure. Having a portable system would allow the surgeon to go from room-to-room and perform the procedure, and thus allow more patients to be treated in a given time period at the clinic.

Biopsy devices are also used with other kinds of X-ray imaging systems such as those for which the patient is upright rather than lying down. The numerous steps described above for locating, confirming, and reconfirming using X-ray stereo "snapshots" are also necessary for the upright versions.

The MAMMOTOME biopsy instrument may also be used with real time handheld imaging devices such as ultrasound imaging devices. When using a biopsy instrument such as the MAMMOTOME with a handheld ultrasound imaging device, the surgeon gains the advantage of having real time imaging of the tissue of interest. Typically the ultrasound imaging device is held in one hand and pointed at the tissue being penetrated by the piercer. In order to facilitate positioning and manipulation of both the biopsy instrument and the imaging device, it is normally necessary to attach the biopsy instrument to a mechanical, articulating arm which is designed to support the weight of the biopsy instrument. In addition, since axial movement of the cutter on the MAMMOTOME is actuated by hand, the biopsy device must be rigidly supported to allow the surgeon to actuate the cutter without moving the tip. Alternatively, an assistant may be used to help operate the controls for the biopsy device. It would, therefore, be advantageous to design a handheld core sampling biopsy instrument wherein the cutter of the instrument was moved using a motor drive which could be actuated by the touch of a switch. Further, since some of the electrical and vacuum controls are not on the MAMMOTOME biopsy instrument itself, the biopsy instrument must be rigidly supported or the surgeon must have an assistant to actuate the controls. It would, therefore, be further advantageous if the electrical and vacuum controls for the biopsy device were positioned in relatively close proximity either on the instrument or, for example, on an associated generator. Automating axial movement of the cutter will, to some extent, eliminate the tactile feedback that the surgeon gets from moving the cutter blade manually. It would, therefore, be advantageous to provide a method of automatically measuring and controlling the axial movement of the cutter which could be utilized to, for example, prevent the cutter from advancing when the port is blocked.

In recent years several patents have issued describing handheld, motorized devices for the extraction of tissue from the body. Many of these devices are for arthroscopic surgery and are not intended for retrieving biopsy core samples of tissue for pathological analysis. The motors are for rotationally driving the cutting/milling end effectors, but not for advancing the end effectors into the tissue. Examples of arthroscopic, handheld, motorized devices include the following U.S. Pat. Nos. 4,995,877; 4,705,038; 5,192,292; 5,112,299; 5,437,630; 5,690,660; and 5,320,635.

In U.S. Pat. No. 4,940,061 issued to Terwilliger, et al, on Jul. 10, 1990, a core sampling, handheld biopsy device incorporating a battery powered motor for driving a means to penetrate and sever tissue is described. The motor axially drives a cutter to advance the cutter into tissue, thus eliminating the noise and jerking associated with mechanical stops of the spring-actuated devices. This significantly adds to the comfort of both the patient and the surgeon. However, the device does not incorporate a vacuum source for obtaining the tissue portion. As described in Burbank, et al, '822 and '333, the vacuum greatly facilitates the capturing of a complete tissue portion within the distal end port on the piercing element. Capturing more tissue with each sample reduces the number of samples required, and increases the likelihood of obtaining the diseased tissue. The Terwilliger device in '061 also does not address how to minimize leakage and spilling of the high volume of fluids present in biopsy procedures.

The surgeon may prefer to use an X-ray imaging system for some patients, and an ultrasound imager for others. In such situations, it would be desirable to use a biopsy instrument which is adaptable to both kinds of imaging systems.

Such an instrument could be used as a handheld instrument or also as an instrument mounted onto the arm of an X-ray stereotactic table, depending on the situation.

It is therefore desirable to provide a more versatile and "patient friendly" biopsy device than what is currently available. The device should be particularly adapted for use without mounting to an X-ray stereotactic table. It should be a lightweight, maneuverable, handheld device, so that the surgeon may have the option to perform the biopsy procedure in combination with an ultrasound imaging device. It is desirable that the device be easily transported from room-to-room so that several patients may be prepared for the surgical procedure concurrently, thus allowing more patients to be treated in a given time period, and potentially reducing the overall cost of the surgical procedure. In addition, it is desirable to perform a biopsy with fewer steps in order to decrease the overall time of the procedure. This would be achievable by eliminating the need to set-up and operate the X-ray stereotactic table. The combination of these factors could allow the surgical procedure to be more widely available to patients than it is currently.

It is also desirable to provide a handheld biopsy device which may be held parallel to the chest wall of the patient, so that suspect tissue masses close to the chest wall can be easily sampled. It is desirable that the surgeon be able to easily steer the penetrating tip of the handheld device towards the desired tissue to be sampled. It is further desired that the surgeon have tactile feedback as the tissue is probed by the penetrating tip of the device, to provide the surgeon with clues regarding the disease state of the tissue encountered. It is also desirable that the biopsy device be "patient friendly" by not having noisy or jerky mechanical actuations during the procedure, and by not having to be used with large machines such as an X-ray stereotactic table.

SUMMARY OF THE INVENTION

The present invention overcomes problems associated with using a biopsy instrument which may be used only when mounted to an X-ray stereotactic system.

In the preferred embodiment, the present invention is a handheld biopsy device which may be used in combination with another handheld imaging device such as an ultrasound imaging device. The biopsy instrument is for the collection of at least one soft tissue sample from a surgical patient. The biopsy instrument has a handpiece which is independently manipulatable by hand movement of the instrument toward and away from the patient. The biopsy instrument has an elongated piercer extending from the distal end of the handpiece. The piercer has a piercer lumen through it and a sharpened distal end for entering tissue when the handpiece is moved independently by hand toward the surgical patient so as to cause the sharpened distal end to penetrate tissue The piercer also has a port located proximal to the sharpened distal end for receiving a portion of a tissue mass when the handpiece is further manipulated independently by hand so as to position the tissue mass adjacent to the port. The piercer lumen is in fluid communication with this port.

The present invention also has an elongated cutter with a lumen through it. This cutter is disposed coaxially and slidably relative to the piercer. The cutter has a cutting blade on the distal end for cutting the portion of tissue protruding into the port of the piercer when the cutter slides distally past the port. A portion of the cut tissue is then deposited within the cutter lumen proximal to the cutting blade.

The present invention includes a cutter rotational transmission contained within the handpiece and operationally connected to the elongated cutter. When the cutter rotational transmission is actuated, the cutter is rotated about its longitudinal axis.

The present invention further includes a cutter axial transmission contained within the handpiece and operationally connected to the elongated cutter. When the cutter axial transmission is actuated, the cutter is slid in an axial direction relative to the piercer. It is slid in the distal axial direction to cut a portion of tissue protruding into the port. It is slid in the proximal axial direction to retrieve the cut portion of tissue from the biopsy instrument.

The biopsy device also has a power transmission source which is operationally engageable with the cutter rotational transmission for rotation of the cutter. In the preferred embodiment, the power transmission source is also operationally engageable with the cutter axial transmission for the longitudinal movement of the cutter. A first electric motor is operationally engaged to the cutter rotational transmission by a first flexible, rotatable shaft. A second electric motor is operationally engaged to the cutter axial transmission by a second flexible, rotatable shaft. The handpiece also includes a holster. The distal ends of the first and second rotatable shafts are rotatably mounted in the holster so that the first and second shafts are operationally engaged, respectively, to the cutter rotational transmission and the cutter axial transmission inside the handpiece.

In the preferred embodiment of the present invention, a tubular tissue remover is disposed in the cutter lumen of the cutter. The tissue remover pushes the tissue portion out of the distal end of the cutter lumen and onto a tissue sampling surface of the handle when the cutter is retracted in the proximal direction. The proximal end of the tissue remover is connected to a first vacuum tube which is connected by a first connector to a fluid collection system. The fluidic contents of the cutter lumen are transported to the fluid collection system when the vacuum is actuated. A strainer on the distal end of the remover is provided to block the tissue portion from entering the remover.

Also in the preferred embodiment, the proximal end of the piercer lumen is connected by a second vacuum tube which is connected by a second connector to the fluid collection system. The fluidic contents of the piercer lumen also are transported to the fluid collection system when the vacuum of the system is actuated.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 6A is a top view in section of the probe assembly and a distal portion of the holster, revealing a cutter in the a first, fully retracted position;

FIG. 6B is a top view in partial section of the distal end of the probe assembly for when the cutter is in the first position and a port on the distal end of a piercer is open;

FIG. 7A is a top view in section of the probe assembly and a distal portion of the holster, revealing the cutter in a third, intermediate position;

FIG. 7B is a top view in partial section of the distal end of the probe assembly and the port on the distal end of the piercer is open in order to receive the tissue portion to be removed from the patient, and a distal blade (shown with hidden lines) of the cutter is immediately proximal to the port, corresponding to the third position of the cutter shown in FIG. 7A;

FIG. 8A is a top view in section of the probe assembly and a distal portion of the holster revealing the cutter in a fourth, fully deployed position;

FIG. 8B is a top view in partial section of the distal end of the probe assembly and the distal blade (shown with hidden lines) of the cutter is shown distal to the port on the distal end of the piercer, corresponding with the fourth position of the cutter tube shown in FIG. 8A;

DETAILED DESCRIPTION OF THE INVENTION

Figure 1:
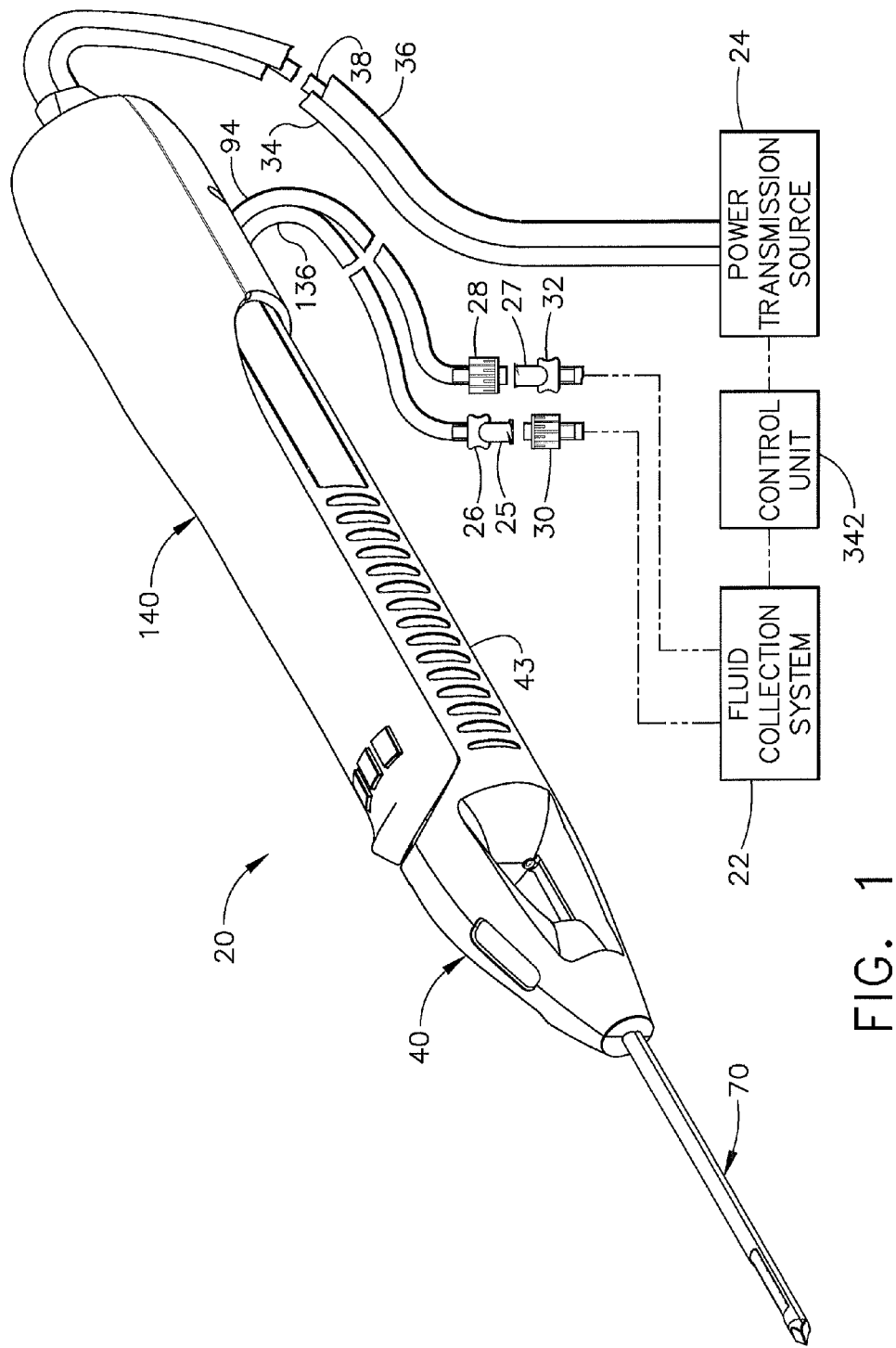
FIG. 1 is an isometric view of the present invention, a biopsy instrument which includes a handpiece for the collection of soft tissue.

FIG. 1 shows a first embodiment of a biopsy instrument comprising a probe assembly 40, a holster 140, a fluid collection system 22, a control unit 342, and a power transmission source 24. The probe assembly 40 is detachably connected to the holster 140. Together they constitute a lightweight, ergonomically shaped, hand manipulatable portion referred to as a handpiece 20. The probe assembly 40 includes a piercer 70 extending distally from a hollow handle 43. The probe assembly 40 is fluidly connected to the fluid collection system 22 by a first vacuum tube 94 and a second vacuum tube 136. The first and second vacuum tubes are detachably connected to the fluid collection system 22 by a first connector 27 and a second connector 25, respectively. The first connector has a male portion 32 and a female portion 28 attached to the first vacuum tube 94. The second connector 25 has a female portion 30 and a male portion 26 attached to the second vacuum tube 136. The connector portions, 26, 28, 30, and 32, are attached in this manner to prevent the accidental switching of the first and second tubes, 136 and 94, to the fluid collection system 22. The holster 140 includes a first rotatable shaft 34, a second rotatable shaft 36, and a control cord 38. The first and second rotatable shafts, 34 and 36, are preferably flexible so that the operator may easily manipulate the handpiece 20 with one hand. The control cord 38 operatively connects the handpiece 20 to the power transmission source 24 and control unit 342.

Since the handpiece 20 is manipulated by the operator's hand rather than by an electro-mechanical arm, the operator may steer the tip of the handpiece 20 with great freedom towards the tissue mass of interest. The surgeon has tactile feedback while doing so and can thus ascertain, to a significant degree, the density and hardness of the tissue being encountered. In addition, the handpiece 20 may be held approximately parallel to the chest wall of the patient for obtaining tissue portions closer to the chest wall then may be obtained when using a instrument mounted to an electro-mechanical arm. As can be seen in FIG. 1, the piercer 70 extends from the distal end of the handpiece 40 and is longitudinally offset with respect to the handpiece 40. This offset also facilitates the insertion of the piercer 70 into the tissue while the axis of the piercer 70 is approximately parallel to the plane of the patient's chest wall. As a result, it is possible to extract tissue portions which are located close to the chest wall of the patient.

Those skilled in the art may appreciate that a mount or "nest" could be provided to hold the handpiece 20 securely to the movable arm of an X-ray stereotactic table or other kind of imaging device which incorporates a movable arm for holding a biopsy instrument. This would provide the operator with the option to use the handpiece 20 to access the tissue mass within the surgical patient in much the same manner as was described earlier for using the MAMMO-TOME instrument. This versatility may be advantageous to the operator, for example, in a situation where the handheld imaging device was temporarily not available for use, and it would be necessary to use the X-ray stereotactic table.

Figure 2:
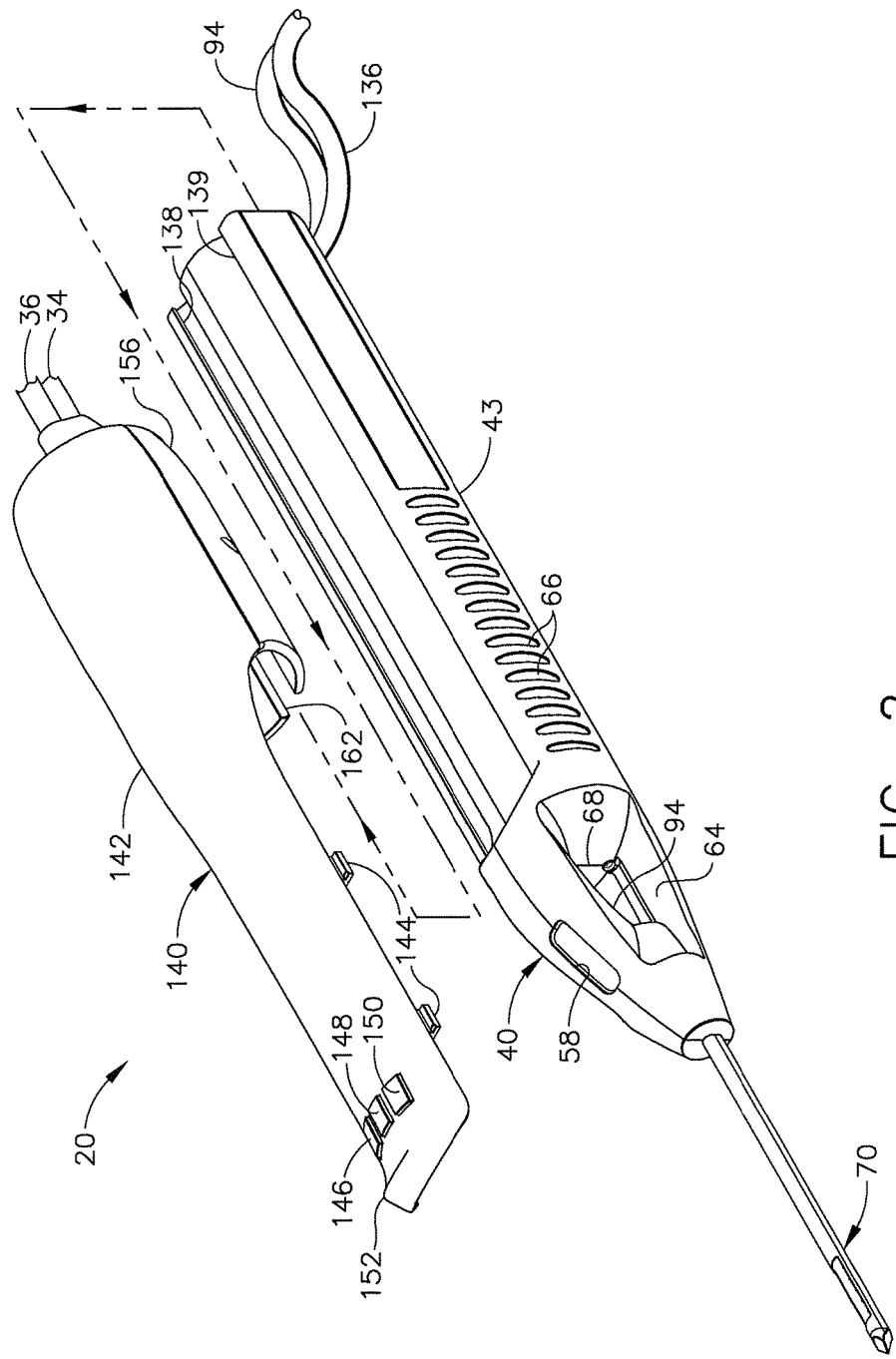
FIG. 2 is an isometric view of the handpiece showing a probe assembly prior to attachment to a holster.

FIG. 2 shows the holster 140 and the probe assembly 40 separated. A pair of tabs 144 project laterally from each side of a holster upper shell 142, and insert into right and left undercut ledges, 138 and 139 respectively, of the hollow handle 43 of the probe assembly 40. A plurality of indentations 66 are provided on the handle 43 to improve the operator's grip on the instrument. A tube slot 162 in the lower shell 156 of the holster L40 provides clearance for first and second vacuum tubes, 94 and 136. A first switch 146, a second switch 148, and a third switch 150 are mounted in the distal portion of the holster 140 so that the physician can operate the handpiece 20 with a single hand while having the other hand free to operate an ultrasonic imaging device or the like. The switches 146, 148, and 150 are provided to operate the power transmission source 24 and the fluid collection system 22 in conjunction with the control unit 342. A ridge 152 on the distal end of the holster 140 is provided to assist the operator in grasping the handpiece 20 and in operating the switches 146, 148, and 150. The ridge 152 further provides the operator with a tactile reference as to where to properly grasp the handpiece 20.

Still in FIG. 2, the probe assembly 40 includes a window 58 so that a portion of the first vacuum tube 94 may be viewed. The first and second vacuum tubes, 94 and 136, are made from a flexible, transparent or translucent material, such as silicone tubing. This enables visualization of the material flowing through the tubes. By having the window 58 in the probe assembly 40, the operator can see the flow in the first vacuum tube 94 without needing to look away from the tissue into which the piercer 70 is inserted. A transverse opening 68 is provided in the distal end of the hollow handle 43 which allows access from either side to a tissue sampling surface 64. The tissue extracted from the surgical patient is retrieved by the operator or an assistant from the tissue sampling surface 64.

Figure 3:
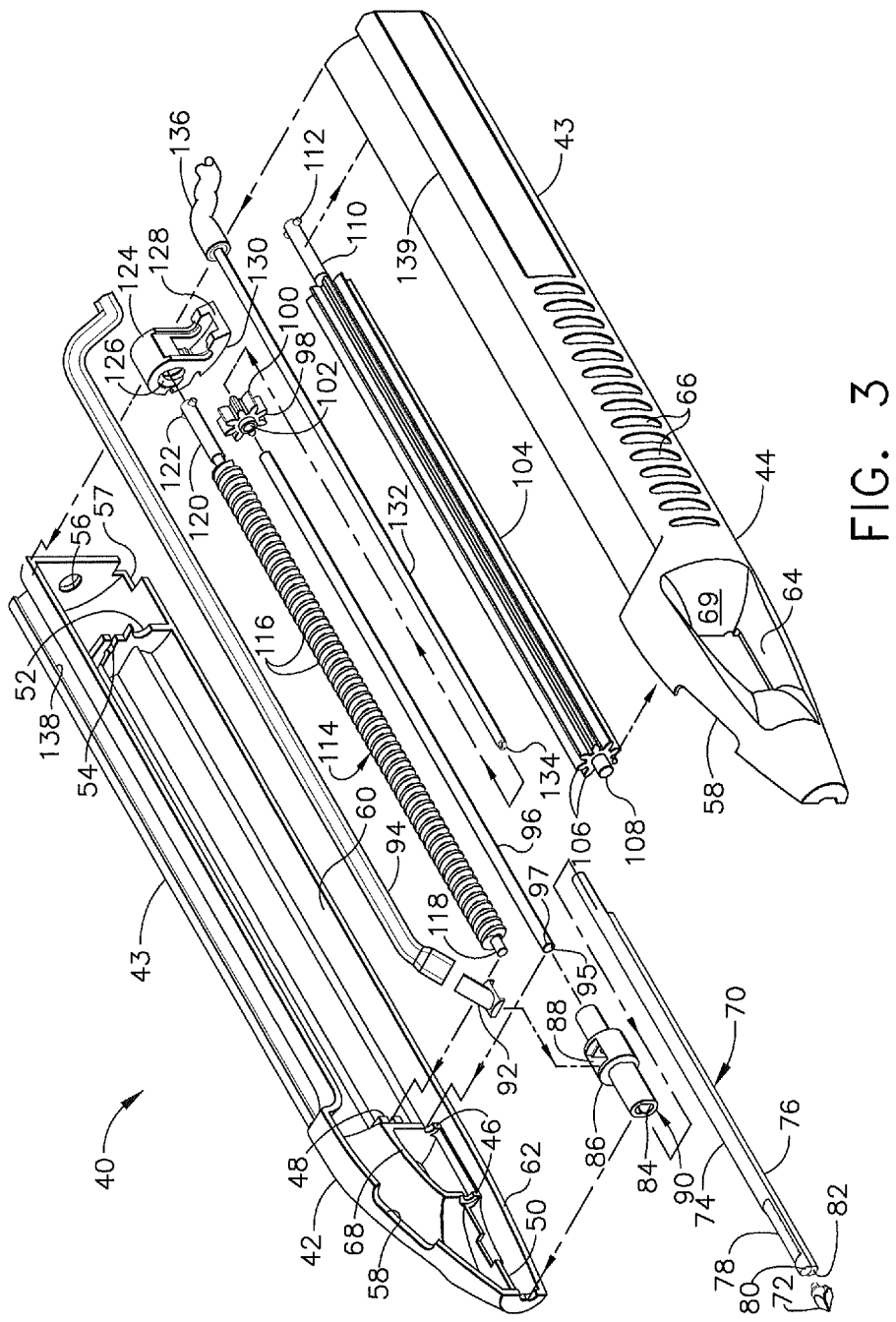
FIG. 3 is an exploded isometric view of the probe assembly.

FIG. 3 is an exploded isometric view of the probe assembly 40. The handle 43 is formed from a right handle shell 42 and a left handle shell 44, each injection molded from a rigid, biocompatible plastic such as polycarbonate. Upon final assembly of the probe assembly 40, the left and right handle shells are joined together by ultrasonic welding along a joining edge 62, or joined by any of several other methods well known in the art. The probe assembly 40 comprises the piercer 70 which includes an elongated, metallic piercer tube 74 having a piercer lumen 80. On the side of the distal end of the piercer tube is a port 78 for receiving the tissue to be extracted from the surgical patient. Joined alongside the piercer tube 74 is an elongated, tubular, metallic vacuum chamber tube 76 having a vacuum lumen 82. Piercer lumen 80 is in fluid communication with vacuum lumen 82 via a plurality of vacuum holes 77 (see FIG. 6B) located in the bottom of the "bowl" defined by the port 78. These holes are small enough to remove the fluids but not large enough to allow excised tissue portions to be removed through the first vacuum tube 94 which is fluidly connected to the vacuum chamber 76. A sharpened, metallic distal end 72 is attached to the distal end of the piercer 70. It is designed to penetrate soft tissue such as the breast. In this embodiment, the sharpened distal end 72 is a three-sided, pyramidal-shaped point, although the tip configuration may also have other shapes.

Still referring to FIG. 3, the proximal end of the piercer 70 is attached to a union sleeve 90 having a longitudinal bore 84 through it, a widened center portion 86, and a transverse opening 88 through the widened center portion 86. The union sleeve 90 is mounted between the left and right handle shells, 44 and 42 respectively, on a pair of union sleeve ribs 50 projecting from each handle shell. An elongated, metallic, tubular cutter 96 is axially aligned within the longitudinal bore 84 of the union sleeve 90 and the piercer lumen 80 of the piercer 70 so that the cutter 96 may slide easily in both the distal and proximal directions. A pair of cutter guides 46 are integrally molded into each of the handle halves, 42 and 44, to slidably retain the cutter 96 in an coaxially aligned position with the proximal end of the piercer tube 74. Cutter 96 has a cutter lumen 95 through the entire length of the cutter 96. The distal end of the cutter 96 is sharpened to form a cutter blade 97 for cutting tissue held against the cutter blade 97 as the cutter 96 is rotated. The proximal end of the cutter 96 is attached to the inside of a cutter gear bore 102 of a cutter gear 98. The cutter gear 98 may be metallic or polymeric, and has a plurality of cutter gear teeth 100, each tooth having a typical spur gear tooth configuration as is well known in the art.

Still in FIG. 3, the cutter gear 98 is driven by an elongated drive gear 104 having a plurality of drive gear teeth 106 designed to mesh with the cutter gear teeth 100. The function of the drive gear 104 is to rotate the cutter gear 98 and the cutter 96 as they translate in both longitudinal directions. The drive gear 104 is preferably made from a metal such as stainless steel. A distal drive axle 108 projects from the distal end of the drive gear 104 and mounts into an axle support rib molded on the inside of the left handle shell 44. A gear shaft 110 projects from the proximal end of the drive gear 104 and is supported by a gear shaft support rib also molded on the inside of the left handle shell 44. A left cross pin 112 is attached to the proximal end of the gear shaft 110 as a means for rotationally engaging the drive gear 104.

Still referring to FIG. 3, a carriage 124 is provided to hold the cutter gear 98 and to carry the cutter gear 98 as it is rotated in the distal and proximal directions. The carriage 124 is preferably molded from a rigid polymer and is cylindrically shaped with a threaded bore 126 through it and with a carriage foot 130 extending from its side. The foot 130 has a recess 128 formed into it for rotatably holding the cutter gear 98 in the proper orientation for the cutter gear teeth 100 to mesh properly with the drive gear teeth 106. The carriage 124 is attached via the threaded bore 126 to an elongated screw 114 which is parallel to the drive gear 104. The screw 114 has a plurality of conventional lead screw threads 116 and is preferably made from a stainless steel. The rotation of the screw 114 in one direction causes the carriage 124 to move distally, while the reverse rotation of the screw 114 causes the carriage 124 to move proximally. In turn, the cutter gear 98 moves distally and proximally according to the direction of the screw rotation, and the cutter 96 is advanced or retracted. In this embodiment, the screw 114 is shown with a right hand thread so that clockwise rotation (looking from the proximal to distal direction) causes the carriage 124 to translate in the distal direction. It is also possible to use a left hand thread for the screw 114 as long as provisions are made to do so in the control unit 342. A distal screw axle 118 and a proximal screw shaft 120 project from the distal and proximal ends, respectively, of the screw 114. The distal screw axle mounts rotatably in a distal screw support 48 of the right handle shell 42 while the proximal screw shaft 120 mounts rotatably in a proximal screw support 54, also in the right handle shell 42. A right cross pin 122 is attached to the proximal end of the screw shaft 120 as a rotational engagement means.

FIG. 3 also shows the first and second vacuum tubes, 94 and 136 respectively, referred to earlier. The distal end of the first vacuum tube 94 is attached to a polymeric vacuum fitting 92 which inserts tightly into the transverse opening 88 of the union sleeve 90. This allows the communication of fluids in the piercer lumen 80 to the fluid collection system 22. The first vacuum tube 94 is contained within the hollow handle 43 in an open space above the screw 114 and drive gear 104, and exits the distal end of the hollow handle through an opening 57. The second vacuum tube 136 is fluidly attached to the proximal end of an elongated, metallic, tubular tissue remover 132. The second vacuum tube 136 exits the hollow handle 43 alongside the first vacuum tube 94 out the opening 57. A strainer 134 is attached to the distal end of the tissue remover 132 to prevent the passage of fragmented tissue portions through it and into the fluid collection system 22. The tissue remover 132 inserts slideably into the tubular cutter 96. During operation of the biopsy instrument, the tissue remover 132 is always stationary and is mounted between a pair of proximal supports 52 on the inside of the right and left handle shells, 42 and 44 respectively. When the cutter 96 is fully retracted to the first position, the distal end of the tissue remover 132 is approximately even with the distal end of the cutter 96. The distal end of the cutter 96 when at its first, fully retracted position, is slightly distal to a vertical wall 69 which is proximal and perpendicular to the tissue sampling surface 64.

In FIG. 3, a right access hole 56 is shown in the proximal end of the right handle shell 43. The right access hole 56 provides access to the proximal end of the screw 114 for operational engagement to the power transmission source 24. Similarly, a left access hole is provided in the left handle shell 44 to provide access to the proximal end of the drive gear 104 for operational engagement with the power transmission source 24.

Figure 9:
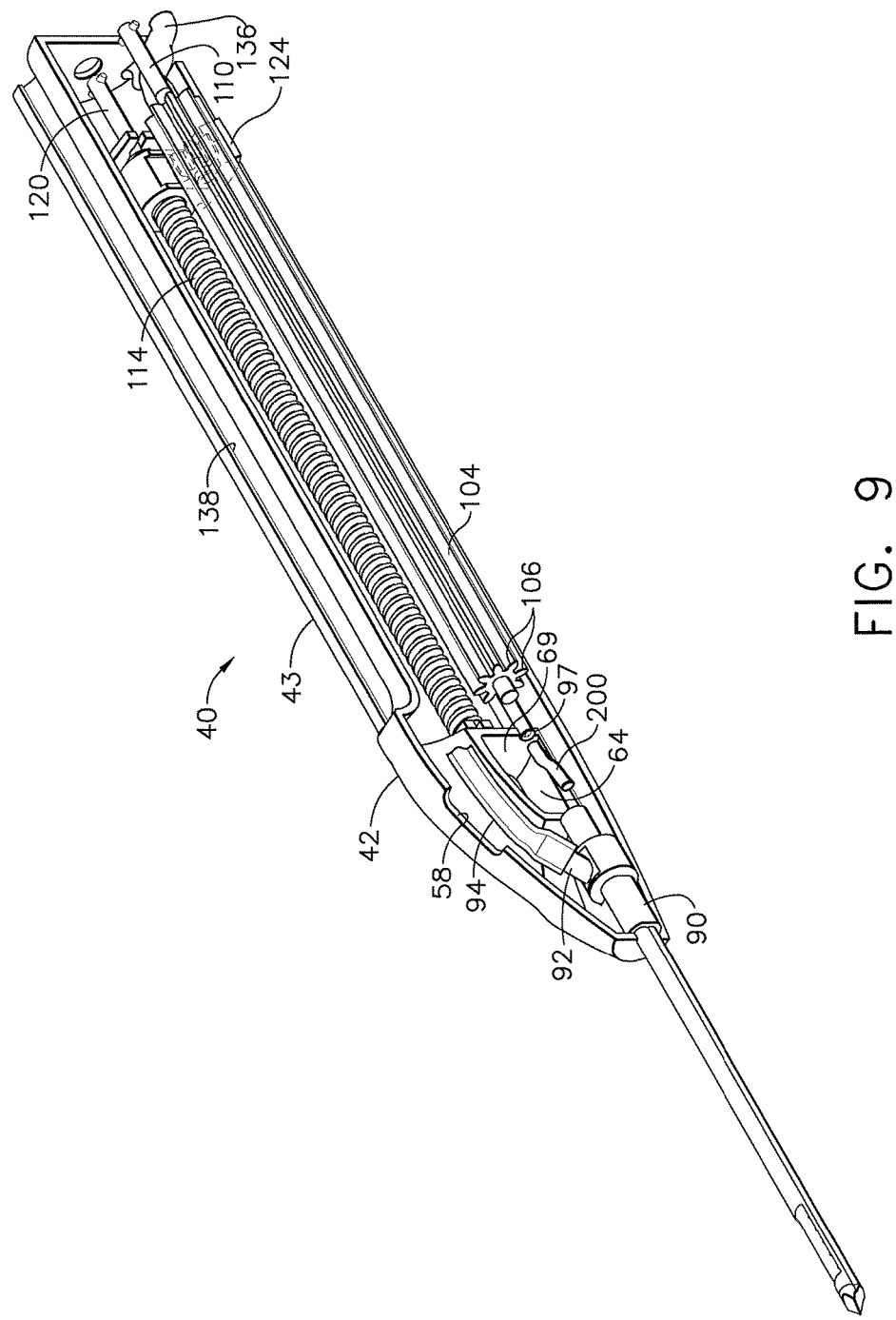
FIG. 9 is an isometric view of the probe assembly with the left handle shell removed, showing the cutter in the first position, and a tissue portion is shown deposited onto a tissue sampling surface of the handle after the tissue portion was removed from the distal end of the cutter.

The tissue remover 132 has two functions. First, it helps to evacuate fluids contained in the piercer lumen 80. This is accomplished by the attachment of the second vacuum tube 136 to the proximal end of the tissue remover 132. Since the distal end of the tissue remover 132 is inserted into the piercer lumen 80, the piercer lumen 80 is fluidly connected to the fluid collection system 22. Second, the tissue remover 132 removes tissue from the cutter 96 as follows. When a tissue sample is taken, the cutter 96 advances to the fourth position just distal to the port 78, and a severed tissue portion 200 is captured within the cutter lumen 95 in the distal end of the cutter 96. Then the cutter 96 translates to the first position so that the cutter blade 97 is just distal to the tissue sampling surface 64. At this position of the cutter 96, the distal end of the tissue remover 132 (which is always stationary) is approximately even with the distal end of the cutter 96. Therefore, any tissue portion of significant size contained within the cutter lumen 95 is pushed out of the cutter lumen 95 and onto the tissue sampling surface 64, as is shown in FIG. 9. The tissue portion 200 may then be retrieved by the operator or an assistant.

Figure 4:
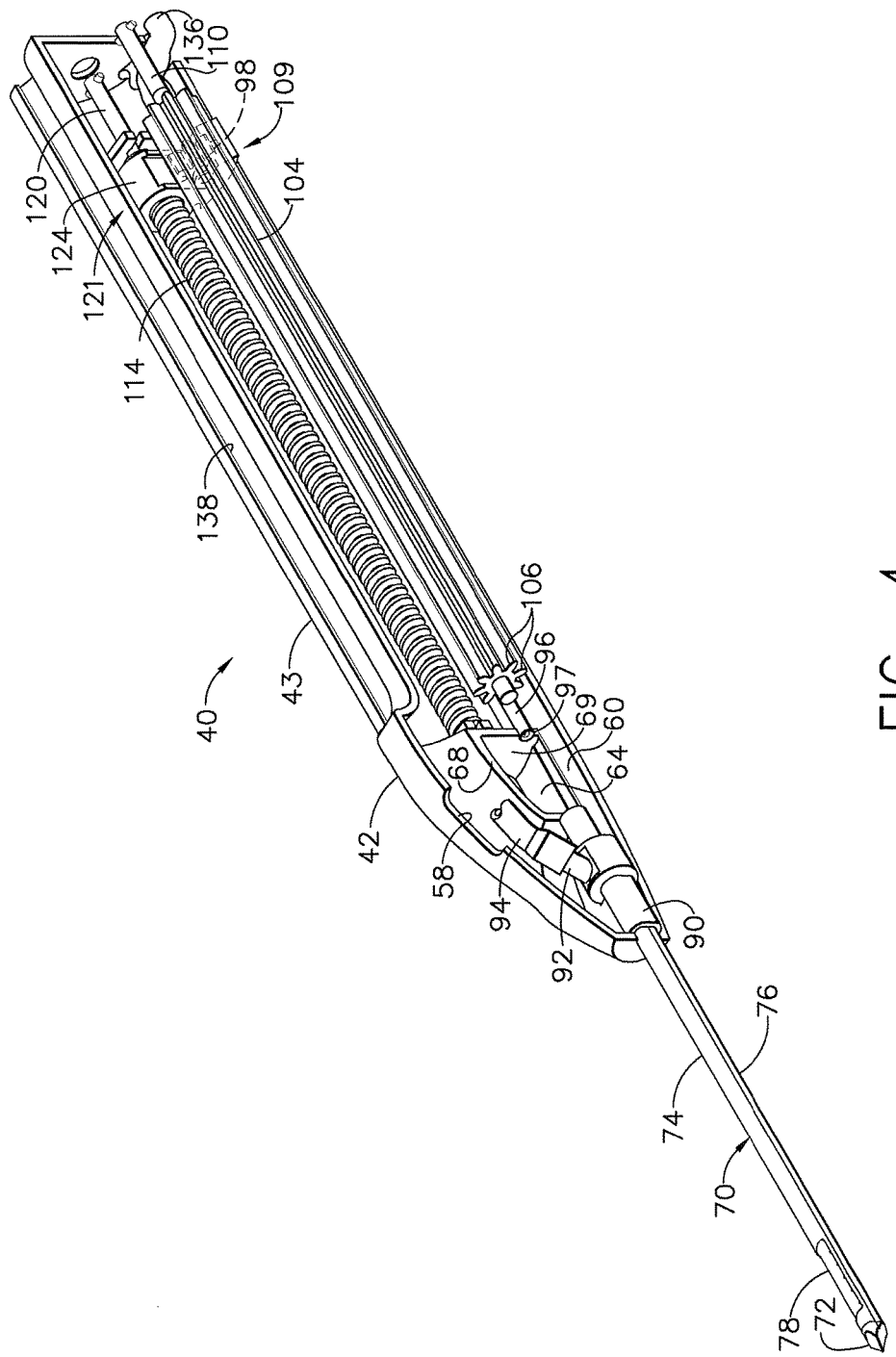
FIG. 4 is an isometric view of the probe assembly of FIG. 2 with the left handle shell removed to reveal the internal components.

Now turning to FIG. 4, an isometric view of the probe assembly 40 with the left handle shell 44 removed reveals the placement of the components described for FIG. 3. Part of the first vacuum tube 94 has also been removed for clarity. The carriage 124 is shown in the fully retracted position so that the cutter 96 is also at the fully retracted, or first position. The cutter blade 97 is slightly distal to the vertical wall 69 on the handle 43. The foot 130 of the carriage 124 is adapted to slide along a carriage guide surface 60 on the inside bottom of the hollow handle 43.

As shown in FIG. 4, a cutter axial transmission 121 includes the carriage 124, the screw 114, and the screw shaft 120. A cutter rotational transmission 109 includes the drive gear 104, the cutter gear 98, and the gear shaft 110.

Figure 5:
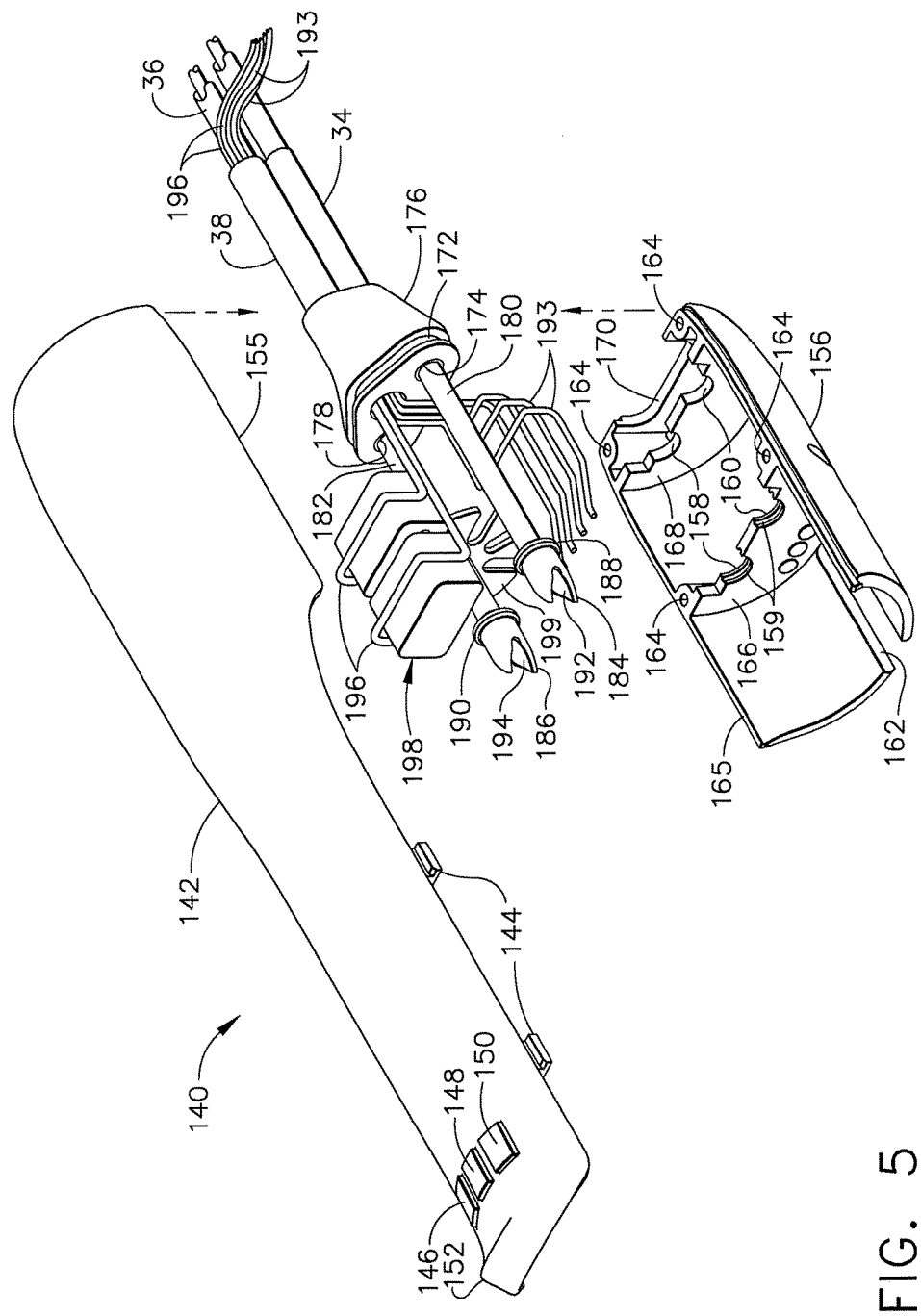
FIG. 5 is an exploded isometric view of the holster.

FIG. 5 is an exploded isometric view of the holster 140 of the first embodiment of the present invention. A holster upper shell 142 and a holster lower shell 156 are each injection molded from a rigid, biocompatible plastic such as polycarbonate. Upon final assembly, the shells are joined together by screws (not shown) or other types of fasteners well known in the art, into a plurality of alignment holes 164. A gear drive shaft 180 and a screw drive shaft 182 are contained within the proximal, enclosed portion of the holster 140. These shafts extend from a grommet 176 which has a groove 172 for retainably mounting onto shell edge 170 of both holster upper and lower shells, 142 and 156, respectively. The grommet 176 rotatably attaches the first rotatable shaft 34 to the screw drive shaft 182 and the second rotatable shaft 36 to the gear drive shaft 180. The first rotatable shaft 34 rotatably inserts into a left bore 172 of the grommet 176. The second rotatable shaft 36 rotatably inserts into a right bore 178. The grommet 176 also provides a strain-relieved attachment of the control cord 38 to the holster 140.

Still referring to FIG. 5, the gear drive shaft 180 is supported rotatably upon a pair of gear drive mounts 160 formed into a first wall 166 and a second wall 168 of the inside of the holster shells, 142 and 156. The screw drive shaft 182 is likewise supported rotatably on screw drive mounts 158. A left coupler 184 is attached to the distal end of the drive gear shaft 180 and has a left coupler mouth 192 for rotational engagement with the left cross pin 112 attached to the gear shaft 110. When the probe assembly 40 shown in FIG. 4 is attached to the holster 140, the gear shaft 110 becomes rotatably engaged to the gear drive shaft 180. This may be seen more clearly in FIG. 6A. Similarly, the screw drive shaft 182 has a right coupler 186 with a mouth 194 which rotatably engages with the cross pin 122 of the screw shaft 120. Each of the left and right couplers, 184 and 186, have a coupler flange, 188 and 190, which rotatably insert into thrust slots 159 formed into the corresponding portions of the drive mounts 158 and 160. These coupler flanges, 188 and 190, bear the axial loading of the drive shafts, 180 and 182.

Still referring to FIG. 5, the holster 140 further includes a screw rotation sensor 198, available from Hewlett-Packard as part number HEDR-81002P, for providing an electronic signal to the control unit 342 to be described in more detail later. In this first embodiment, the rotation sensor 198 is mounted within the inside of the holster upper shell 142 and in a position directly above the screw drive shaft 182. A fluted wheel 199 is attached to the screw drive shaft 182 and extends in front of a light emitting diode contained within the rotation sensor 198. As the fluted wheel 192 rotates, the interrupted light beams are electronically detected and transmitted back to the control unit 342 to provide information about the rotational speed of the screw drive shaft (cutter tube axial advancement or retraction speed), and the number of screw rotations from the beginning of operation (instantaneous axial position of the cutter 96). The rotation sensor leads 196 pass through the grommet 176 and are part of the bundle of conductors within the control cord 38.

The holster 140 of the first embodiment of the present invention has the switches, 146, 148, and 150, mounted on the inside of the holster upper shell 142. The switches, 146, 148, and 150, are electronically connected to a plurality of conductors 193 contained in the control cord 38. In one embodiment, the third switch 150 operates the fluid communication between the handpiece 20 and the fluid collection system 22 and also sets the control unit 342 to respond to various commands; the second switch 148 operates the movement of the cutter 96 in the proximal direction and sets the control unit 342 to respond to various commands; the first switch 146 operates the movement of the cutter 96 in the distal direction and sets the control unit 342 to respond to various commands. The functions of the switches, 146, 148, and 150, are not restricted to what has been described for the first embodiment. Also, the physical locations of the switches, 146, 148, and 150, on the handpiece 20 are not restricted to the locations depicted in FIG. 2. Other embodiments of the handpiece 20 of the present invention may incorporate certain ergonomic or other considerations, and the switches, 146, 148, and 150, may be located elsewhere.

FIGS. 6A through 8A depict three of the four positions of the cutter 96 during the operation of the present invention as embodied in the prior FIGS. 1-5. The three positions are most easily distinguished by observing the relative positions of the carriage 124 and the cutter blade 97 of the cutter 96.

In FIGS. 6A and 6B, the retracted, first position is depicted with the carriage 124 located on the proximal ends of the drive gear 104 and the screw 114. The cutter blade 97 is shown to be immediately proximal to the tissue sampling surface 64. In this first position, the tissue portion 200 may be retrieved from the tissue sampling surface 64 as depicted in FIG. 9.

The second position of the cutter 96 is not shown in the Figures. At the second cutter position, the distal end of the cutter 96 is just distal to the tissue sampling surface 64 and inside the piercer lumen 80 near the proximal end of the piercer tube 74. During operation the cutter 96 is moved from the first position to the second position at a slower axial speed than from the second position to the third position in order to facilitate the insertion of the cutter 96 into the proximal end of the piercer lumen 80.

In FIGS. 7A and 7B, the cutter 96 is shown in the third position. The carriage 124 is shown to have moved axially to the intermediate position which is a short distance from the distal ends of the screw 114 and the drive gear 104. The cutter blade 97 is shown by hidden lines to be located just proximal to the port 78. The vacuum holes 77 are open to the port 78 so that soft tissue adjacent to the port 78 prolapses into the port 78 when the first vacuum tube 94 is fluidly connected to the vacuum of the fluid collection system 22.

FIGS. 8A and 8B shows the cutter 96 at the fourth position, and the carriage 124 is located near the distal ends of the screw 114 and the drive gear 104. The cutter blade 97 is shown now (by hidden lines) to be distal to the port 78 and to be covering the vacuum holes 77. The tissue pulled into the port 78 will have been severed by the rotating, advancing cutter blade 97 and stored inside the cutter lumen 95 of the distal end of the cutter 96. When the cutter 96 retracts back to the first position as shown in FIGS. 6A and 6B, the tissue portion 200 may be retrieved as shown in FIG. 9.

Figure 10:
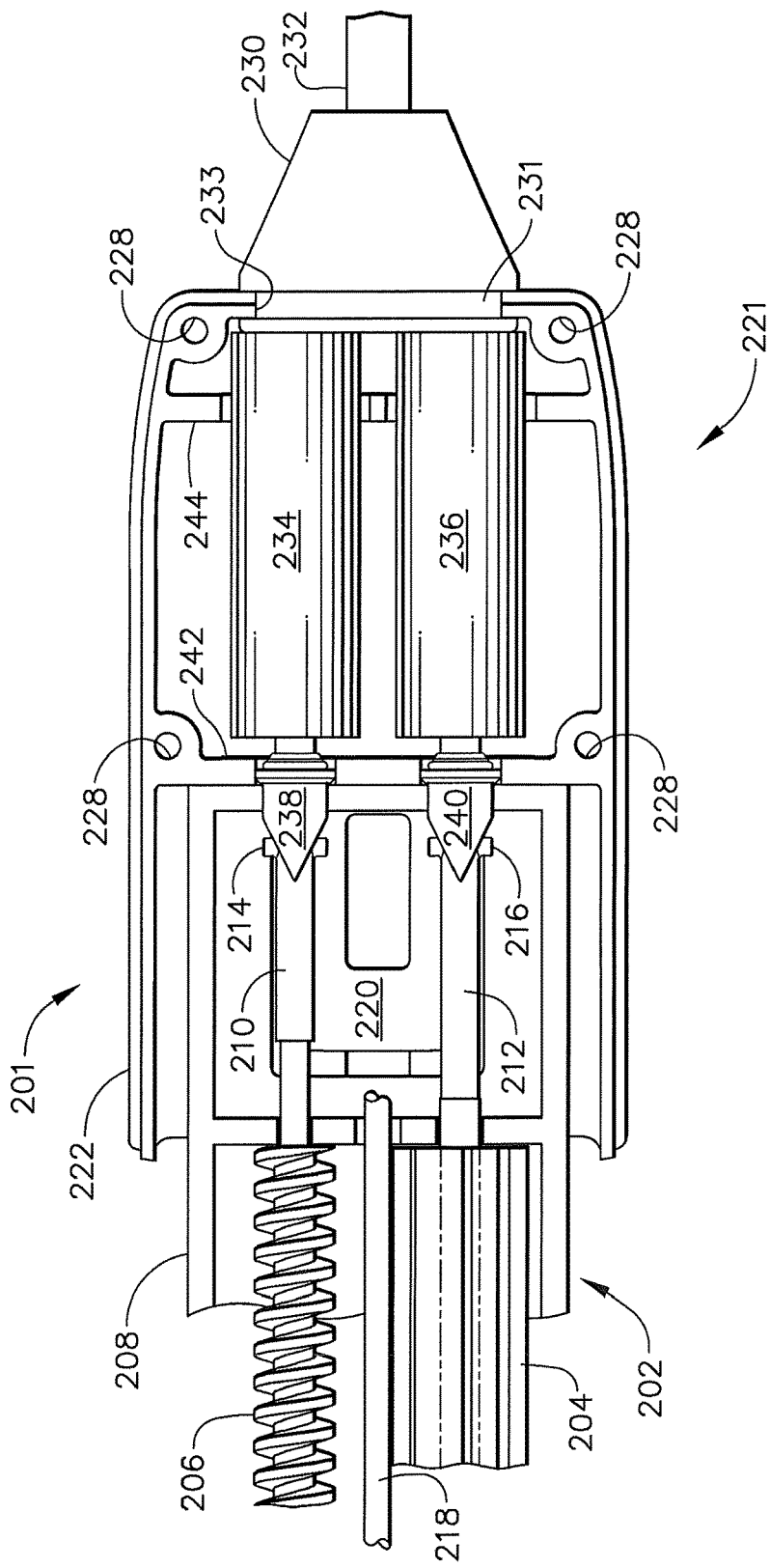
FIG. 10 is a partial top view of a second embodiment of the present invention, wherein a holster upper shell and a probe assembly upper shell have been removed to reveal the internal components.

FIG. 10 shows a second embodiment of the present invention. The main difference from the first embodiment is that in the second embodiment a first and a second brushless, electric motor, 234 and 236 respectively, are mounted inside a holster 221. First and second motors, 234 and 236, are available from Harowe Servo Controllers, Inc., part number B0508-050. In this second embodiment, the rotatable shafts 34 and 36 have been eliminated so that only a control/electrical power cord 232 is required to electrically connect the holster 221 to the power transmission source 24 and the control unit 342 (see FIG. 1). A holster lower shell 222 has a first wall 242 and a second wall, 244, which are spaced apart and adapted to support the pair of electric motors, 234 and 236 in a side-by-side arrangement. The use of the brushless electric motors, 234 and 236, eliminates the need for a separate rotation sensor to be mounted in the drive train of one or both of a screw 206 and a drive gear 204 as was described for the first holster embodiment shown in FIG. 5. As in the first embodiment, when a probe assembly 202 is attached to the holster 221, a right coupler 238 rotationally engages a right cross pin 214 of a screw shaft 210. A left coupler 240 rotationally engages a left cross pin 216 of a gear shaft 212. A grommet 230 having a grommet groove 231 is retained by an attachment slot 233 in the holster shell 222. Fastener holes 228 are provided to fasten the holster lower shell 222 to a holster upper shell using screws or other types of fasteners well known in the art.

Still referring to FIG. 10, another difference of the second embodiment compared to the first is that the probe assembly 202 comprises a lower shell 208 and an upper shell (removed for clarity) whereas the hollow handle 43 of the first embodiment shown in FIGS. 1-4 was divided vertically into left and right shells, 44 and 42 respectively. This embodiment facilitates the addition of a probe latch 220 and other features shown in FIG. 11.

Using conventional techniques well known in the art, it is possible to use only one electrically driven motor in place of the two motors described for both the first and second embodiments of the present invention. That is, a single motor may be used to both rotate and advance the cutter 96. The motor may be incorporated into the instrument so that the cutter rotation and cutter advancement (axial movement) may occur either simultaneously or separately. The motor may be located within the adapted handpiece 40 and be electrically connected to the power source 24 and the control unit 342. The motor may also be outside the handpiece 40, still electrically connected to the power source 24 and the control unit 342, and mechanically engaged to the handpiece 40 by a single flexible shaft.

Figure 11:
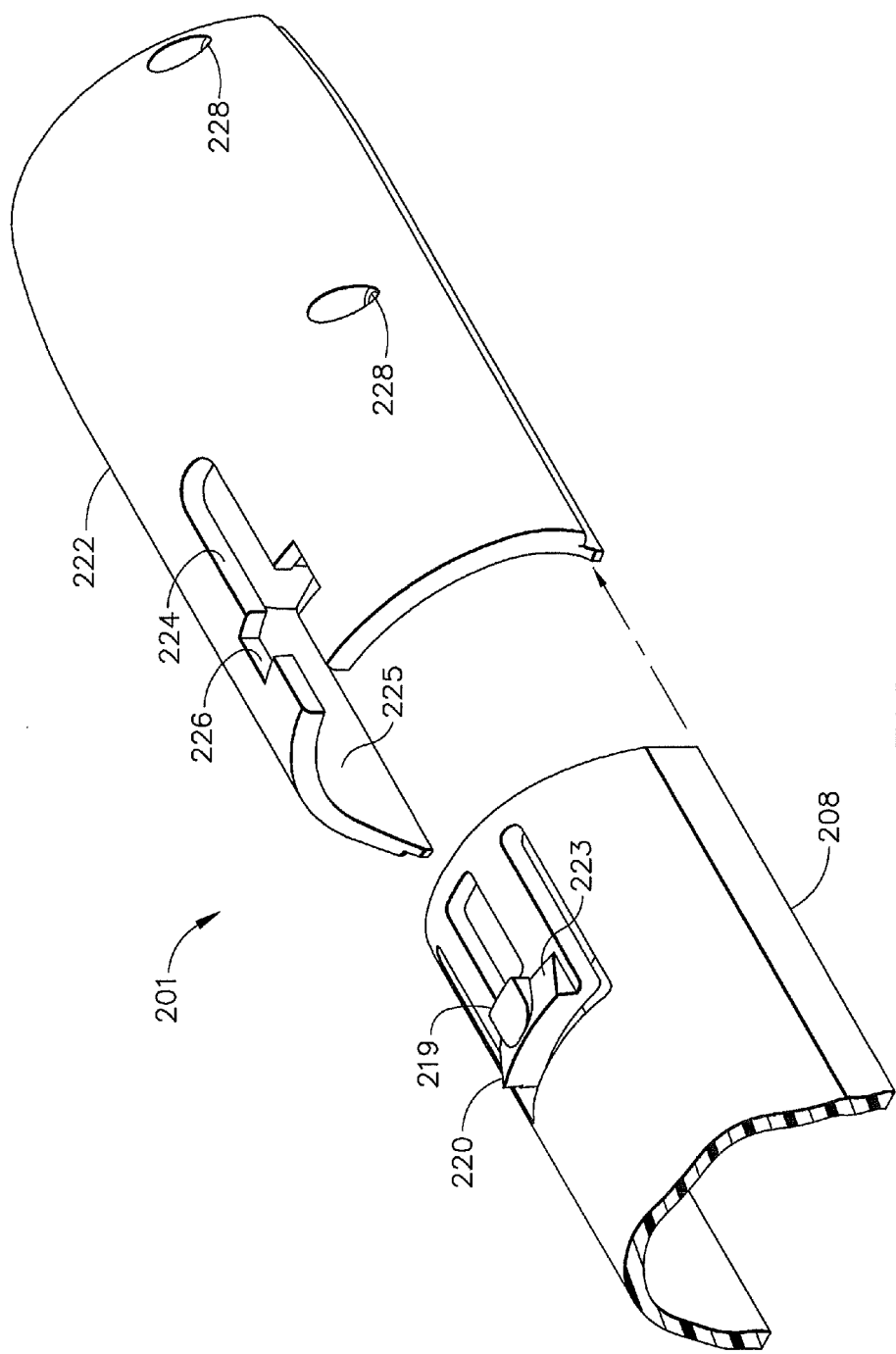
FIG. 11 is an isometric view of a holster lower shell and part of a probe assembly lower shell of the biopsy instrument shown in FIG. 10 revealing a latch and a holster slot.
Figure 12:
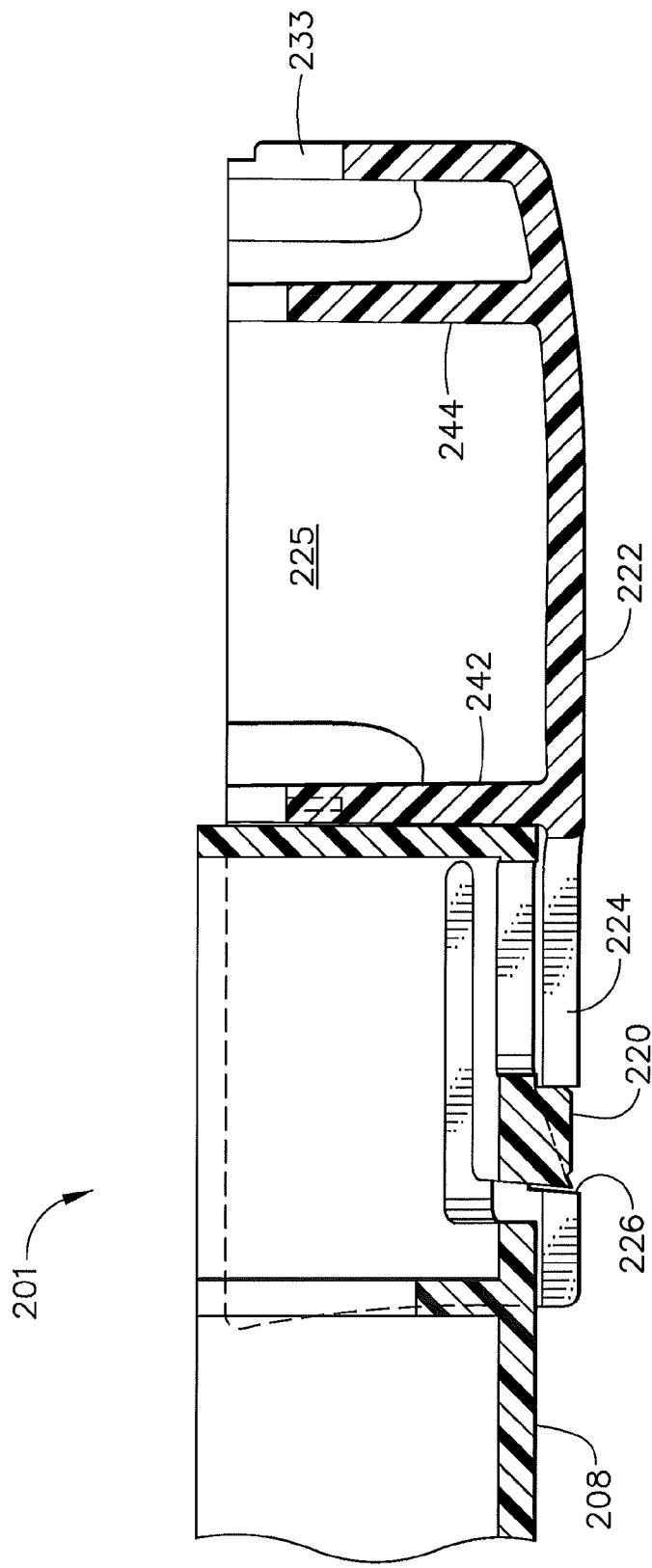
FIG. 12 is a longitudinal section of the assembled components of FIG. 11.

FIG. 11 shows an isometric view of the probe lower shell 208 and the holster lower shell 222 of the biopsy instrument 201 of the second embodiment of the present invention. The view is shown with the bottom side up in order to clearly present a probe latch 220 which is molded as a cantilever into the probe lower shell 208, and can be deflected downwards by a force applied to a latch ramp surface 223. The latch 220 further comprises a latch projection 219 for insertion into a holster slot 224 as the probe assembly is inserted into the holster 221. The ramp surface 220 is deflected downwards by interaction with an inside surface 225 of the holster shell 222 and retainably snaps into a slot key 226 when the probe assembly is fully inserted into the holster, thus rotationally engaging the left and right couplers, 240 and 238, to the drive shaft 212 and the gear shaft 210, respectively, as shown in FIG. 10. To remove the probe assembly from the holster, one must press on the projection 219 while pulling them apart. FIG. 12 shows a longitudinal section through the center axis of the probe lower shell 208 and the holster lower shell 222 of FIG. 11 for when they are fully attached together.

Figure 13:
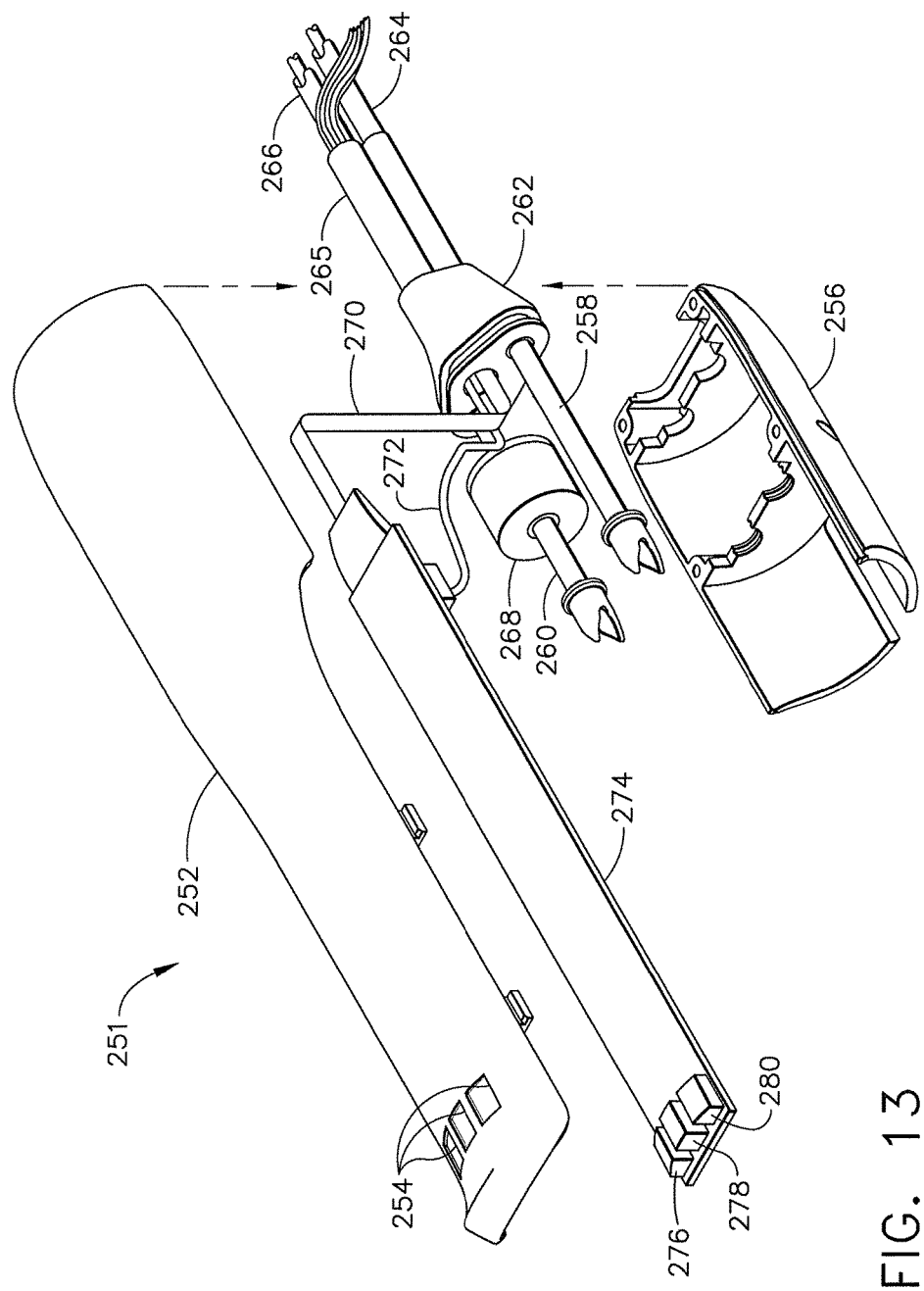
FIG. 13 is an exploded isometric view of a holster of a third embodiment of the present invention, showing a switch board and a rotation sensor.

FIG. 13 is an exploded isometric view of a holster 251 of a third embodiment of the present invention. It may be used with the probe assembly 40 of the first embodiment shown in FIG. 14. A first and a second rotatable shafts, 264 and 266, are attached by a grommet 262 to a drive shaft 258 and a screw shaft 260, respectively. Rotatable shafts, 264 and 266, are preferably flexible too, in order for the holster 251 combined with the probe assembly 40 (see FIG. 2) to be easily manipulatable with one hand. A fully integral rotation sensor 268 is shown mounted on a screw shaft 260. This rotation sensor 268 is a miniature optical encoder which is commercially available as Model Number SEH17 from CUI Stack, Inc. It is electrically connected to a switch board 274 which mounts to the inside of the holster upper shell 252. The switch board 274 also has a ribbon cable 270 containing a plurality of conductors for conveying electronic information to and from the control unit 342, power transmission source 24, and the fluid collection system 22, via a control cable 265. The switch board 274 has mounted on its distal end, three switches, 276, 278, and 280, for operation of the present invention in the same manner as described in the first embodiment: a third switch 280 for fluidic connection to the vacuum of the fluid collection system; a first switch 246 for the forward movement of the cutter 96; and a second switch 248 for the reverse movement of the cutter 96. The specific functions of the switches, 276, 278, and 280, are not restricted, in other possible embodiments of the present invention, to the functions described, nor to the physical locations shown. The switches, 276, 278, and 280, project through switch openings 254 of the holster upper shell 252. A holster lower shell 256 attaches to the upper shell 252 as in the other embodiments to enclose the components of the proximal portion of the holster 251.

Those skilled in the art could easily appreciate that the switch board 274 and the three switches, 276, 278, and 280, may instead be incorporated into a foot operable device rather than in the hand operable holster 251 shown in FIG. 13. The operator would still be able to manipulate the instrument with a single hand while actuating the switches, 276, 278, and 280, by foot, thus freeing the other hand for holding the ultrasound imaging device, or for performing other steps in the surgical procedure.

Figure 14:
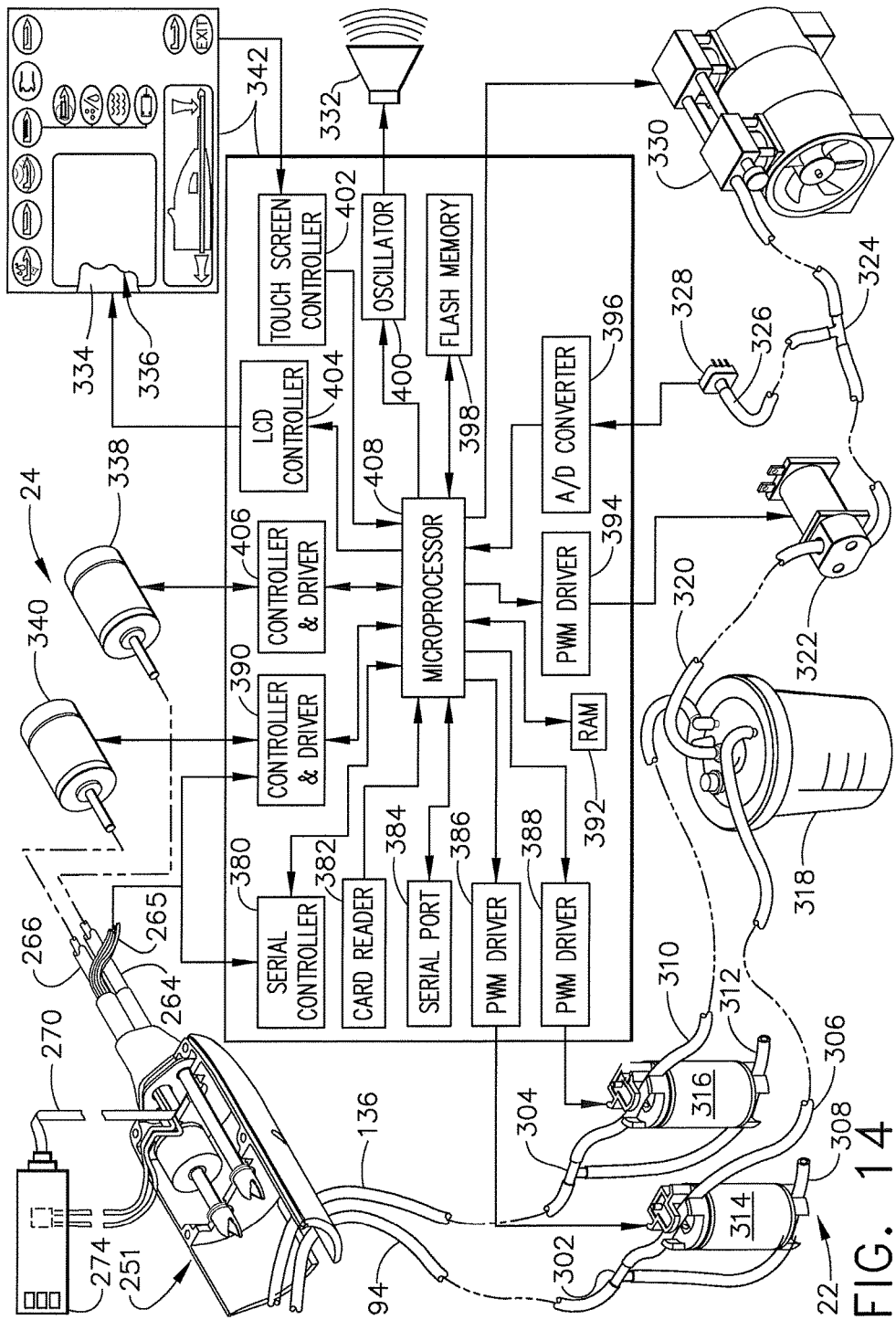
FIG. 14 is a schematic diagram of a control unit and its relationship to the other components of the present invention.

FIG. 14 shows the relationship of the electro-mechanical components of the present invention to the control unit 342. The third embodiment of the present invention is depicted and includes the holster 251 of FIG. 13. A first motor/tachometer combination 338 (sometimes referred to as a first motor/tach) and a second motor/tachometer combination 340 (sometimes referred to as a second motor/tach) are depicted as part of the power transmission source 24, and transmit rotational power to the holster 251 via the first and second rotatable shafts, 264 and 266, respectively. The motor/tach combinations, 340 and 348, are commercially available as DC MicroMotors Series 3863, MicroMo Electronics, Inc. The control cord 265 is electrically connected to a serial controller 380 available as Part No. MCF5206eFT40 from Motorola, Inc. A serial controller 380 is electronically connected to the switchboard 274 by ribbon cable 270 and control cord 265. The serial controller 380 coordinates information exchange across the serial communication link between the switchboard 274 and the microprocessor 408. An advantage provided by the use of the serial controller 380 is that the required number of conductors 193 may be reduced.

FIG. 14 depicts the interconnection of the electro-mechanical components of the fluid collection system 22 and power transmission source 24 with control unit 342. The first vacuum tube 94 coming from the probe assembly 40 (see FIG. 2) is attached to a first vacuum Y-connector 302 fluidly connected a first upper line 306 and a first lower line 308.

The two lines, 306 and 308, pass through a first pinch valve 314. A suitable, commercially available, three-way pinch valve for this application is Model Number 373 12-7 15 available from Angar Scientific Company, Inc. The pinch valve 314 closes either the upper line 306 or the lower line 308, but never both lines simultaneously. The lower line 308 provides a vent to atmospheric pressure. The upper line 306 attaches to a fluid collection canister 318. Similarly, the second vacuum line 136 from the probe assembly 40 attaches to a second Y-connector 304 which fluidly is connected to a second upper line 310 and a second lower line 312. The first and second vacuum Y-connectors, 302 and 304, are molded from a rigid polymer such as polycarbonate The second upper line 310 passes through a second pinch valve 316, which is identical to the first, and to the canister 318. The second lower line 312 passes through the second pinch valve 316 and vents to atmosphere. Again, only one or the other of the two lines may be pinched closed at any time.

Still referring to the fluid collection system of FIG. 14, a main vacuum line 320 attaches the canister 318 to an electrically powered vacuum pump 330. A suitable vacuum pump for this application is available by the trademark name WOB-L PISTON Series 2639, from Thomas Compressors and Vacuum Pumps. The main vacuum line 320 passes through a regulator valve 322 to electronically adjust the vacuum pressure supplied to the canister 318. A commercially available regulator valve for this application is model number VSONC 6 S 11 V H Q 8 from Parker Hannifin Corp., Pneutronics Division. A pressure sensor 328 is fluidly attached to the main vacuum line 320 at a sensor connection 324. The signal from the pressure sensor 328 is sent to an A/D converter 396 of the control unit 342. A commercially available, compensated pressure sensor for this application is model number SDX15 from SenSym, Inc.

At the heart of the control unit 342 is a 40 MHz, 32 bit microprocessor 408, available from Motorola, Inc. as Part No. MCF5206EFT40, which is designed to perform logic operations that eventually translate into simple electromechanical actions.

Still referring to FIG. 14, the control unit 342 includes a 640.times.480 color TFT-LCD display 334 available from Sharp as part number LQ64D343. Display 334 is covered by a resistive touchscreen 336 for the user interface. The touch screen 336 is available from Dynapro as part number 95638, and is electronically connected to a touch screen controller 402 in the control unit 342. The touchscreen controller 402 interfaces with the microprocessor 408 and comprises the following: a microcontroller, part number PIC16C58A, available form Microchip; an EEPROM, part number 93AA466SN, available from Microchip; an A-D converter, part number TLV1543CDW, available from Texas Instruments; and a multiplexer-demultiplexer, part number MC74HC4052D, available from Motorola. The touch screen controller allows the control unit 342 to respond to the user's touch by interpreting touch inputs. Similarly, an LCD controller 404 is an interface between the microprocessor 408 and the LCD display 334. The LCD controller 404 reduces the burden of the microprocessor 408 by efficiently controlling display parameters such as color, shading, screen update rates, and it typically accesses the memory chips of the microprocessor 408 directly. The LCD controller 404 comprises the following: a LCD controller, part number SED1354FOA, available from Epson; a display buffer DRAM, part number MT4LC1M16E5TG-6, available from Micron; and a line driver, part number 74ACTQ16244SSCX, available from National.

A miniature annunciator 332 is provided with the control unit 342 in order to provide the user with audible, feedback "beeps" upon each activation of an icon control on the LCD display 334. A suitable annunciator for this application is model number EAS-45P104S from Panasonic (Matshusita Electric Corp. of America). The annunciator 332 interfaces with the microprocessor 408 by an oscillator 400 which converts the digital input signal from the microprocessor 408 to an analog, periodic output signal, thus controlling the audio frequency of the speaker. The volume of the sound coming from the annunciator 332 is controlled by a programmable attenuator. The oscillator 400 comprises the following: a 8 MHz oscillator, part number ASL-8.0000000-PCSA, available from AMD; and a PLD, part number EPM7256ATC144-7, from Altera.

Still referring to the schematic diagram of FIG. 14, a first motor controller and driver 390 interfaces the second electric motor/tach 340 with the microprocessor 408. The first motor controller and driver 390 comprises the following: an H-bridge, part number LMD18200T, available from National; a motion controller, part number LM629M-8, available from National; and a PLD, part number EPM7256ATC144-7, available from Altera. The second motor/tach 340 is operationally connected to the second flexible shaft 266 for the actuation of the cutter axial transmission 121 (see FIG. 4). The controller and driver 390 converts digital input signals from the microprocessor 408 into analog motor input signals for controlling motor rotational direction and speed. A closed loop digital speed control of the motor is also achieved within the controller and driver 390 using feedback signals from the rotation sensor 268 available from CUI Stack, Inc., as part number SEH17 (see FIG. 13). The first electric motor/tach 338 drives the cutter rotational transmission 109 (see FIG. 4) via the first rotatable shaft 264. The first electric motor/tach 338 interfaces with the microprocessor through the second controller and driver 406.

An optional card reader 382 may be provided in the control unit 342 for reading data from memory card in order to facilitate future software upgrades and servicing.

A serial port 384 is provided for the bidirectional data exchange in a serial transmission mode, again to facilitate future software upgrades and servicing. The serial port 384 comprises the following: a UART, part number ST16C2552CJ44, available from EXAR; and a line driver-receiver, part number DS14C335MSA, available from National.

A first PWM (pulse width modulation) driver 386 interfaces the first pinch valve 314 with the microprocessor 408. The first PWM driver 386 converts a digital input signal from the microprocessor 408 to an analog output signal having a wave of fixed frequency and amplitude, but varying duty cycle. To drive the solenoid in the pinch valve 314, the PWM driver 386 is used when the duty cycle is high to initially move the solenoid. Once the pinch valve 314 is actuated, the duty cycle is reduced to a level which maintains valve position, thus minimizing power requirements. A second PWM driver 388 similarly interfaces a second pinch valve 316 with the microprocessor 408. A third PWM driver 394 interfaces with the regulator valve 322. The PWM drivers, 394, 388, and 386 each comprise the following: a PLD, part number EPM7256ATC144-7, available from Altera; and a FET transistor, part number NDS9945, available from Fairchild.

A RAM memory device 392 available from Micron as DRAM part number MT4LC1M16E5TG-6, is provided with the microprocessor 408, and inherently loses stored data when power is removed. A flash memory device 398, on the other hand, is provided with the microprocessor 408 to store data even without continuous power, but it has slower access time than the RAM device 392. The flash memory device 398 is part number Am29LV800BT-70REC from AMD.

An A/D converter 396 converts voltage signals from the pressure sensor 328 into digital signals to the microprocessor 408, for maintaining the desired vacuum pressure in the fluid collection system 22. The A/D converter 396 is part number PCF8591AT, available from Philips.

Still referring to FIG. 14, the first (axial) controller and driver 390 and the second (rotational) controller and driver 406 continually calculate and update the axial and rotational position of the cutter 96 within the handpiece 20. They also calculate the speed and acceleration of the cutter 96 axial and rotational movement from the positional information. The microprocessor 408 monitors both the axial position and speed of the cutter 96 and the rotational position and speed via the first controller and driver 390 and the second controller and driver 406.

While in the sampling mode and with the cutter 96 advancing toward the third position (proximal to port 78), when the cutter 96 reaches a predetermined axial position, the microprocessor 408 sends a signal to the second controller and driver 406 to initiate cutter rotation. The rotational speed of the cutter 96 follows a predefined speed profile which insures that the cutter rotational speed is at Z revolutions per minute (rpm) when the cutter 96 reaches the third position. When the cutter 96 reaches the third position, the microprocessor 408 sends a signal to the first controller and driver 390 to advance the cutter 96 at speed Y. The cutter 96 then progresses through the port 78 at advancement speed Y while rotating at velocity Z. While advancing through the port 78, the cutter rotational speed is monitored by the second controller and driver 406. If the rotational speed is greater than Z rpm, electrical current to the first (cutter rotation) motor/tach 338 is decreased. If the cutter rotational speed is less than Z rpm, electrical current to the first motor/tach 338 is increased. One method of performing the speed control on both the first and second motor/tach's, 338 and 340, is to generate an error signal based on the difference between the desired speed and the actual speed. The error signal is then input into a proportional, differential, and derivative (PID) digital filter which is part of the respective controller and driver, either 390 or 406. The sum of these three terms is used to generate the pulse width modulation (PWM) signal. The generation of the error signal and the PWM signal is accomplished by the first and second controllers and drivers, 390 and 406. A PWM signal is input to the first controller and driver 390 to generate an analog output signal to drive the first motor/tach 338. Similarly, a PWM signal is input to the second controller and driver 406 to generate an analog output signal to drive the second motor/tach 340.

The microprocessor 408 also monitors the output value of the second controller and driver 406 PID filter such that if it exceeds a predefined maximum value, it will reduce the axial speed of the cutter 96 a set amount by sending an updated speed command to the first controller and driver 390. This closed-loop algorithm is intended to insure that the target rotational speed is attained by decreasing the axial speed of the cutter 96 under maximum loading conditions. The control logic then repeats from the beginning.

Figure 15:
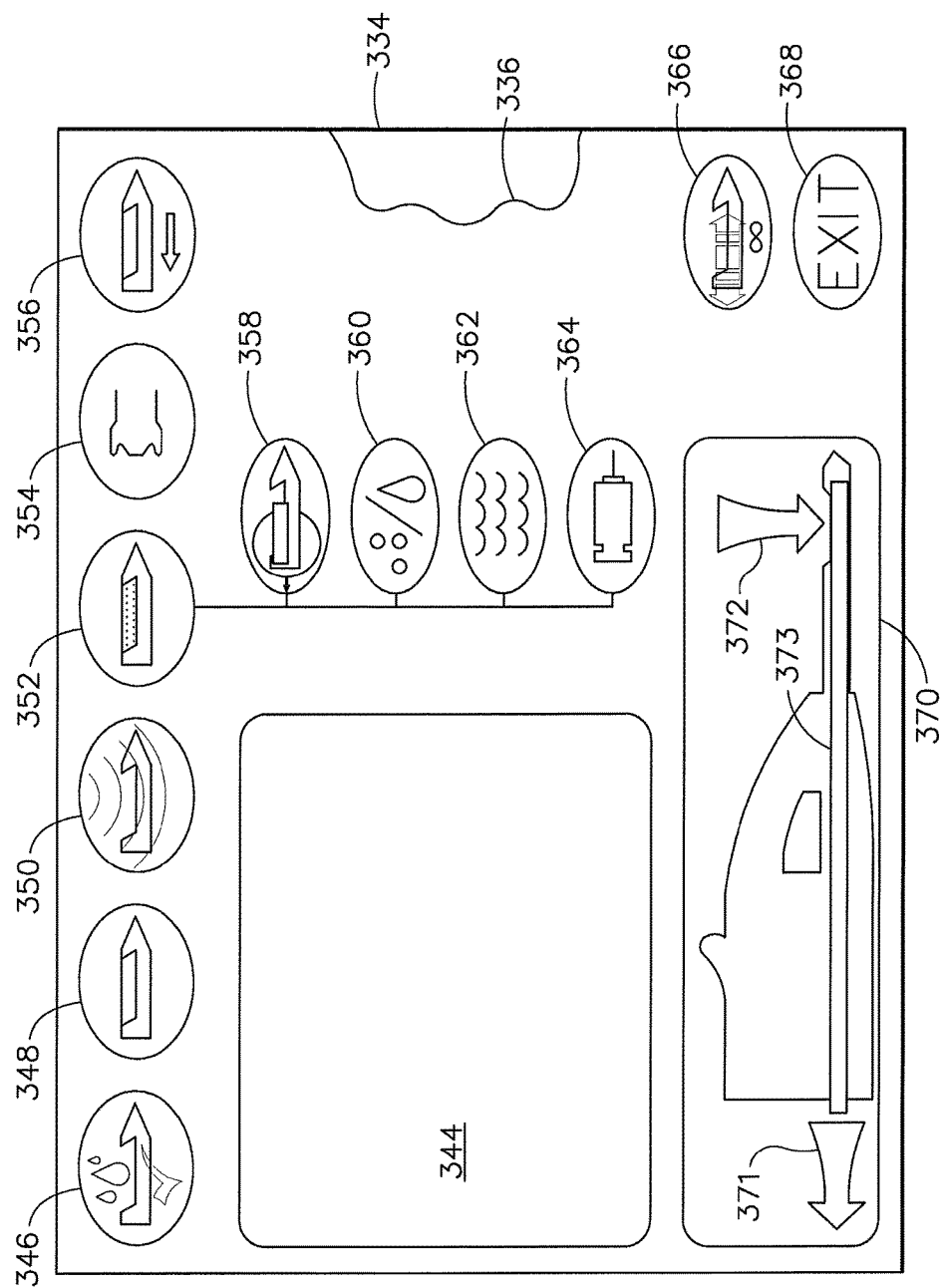
FIG. 15 is an enlarged diagram of the display illustrated in FIG. 14.

FIG. 15 is an enlarged view of the LCD display 334 and the touch screen 336, shown as part of the control unit 342 of FIG. 14. In one embodiment of the present invention, twelve separate operating modes are available to a user. A control switch for each operating mode is displayed graphically on LCD display 334 in the form of icons, 346, 348, 350, 352, 354, 356, 358, 360, 362, 364, 366, and 368. The user may initiate a particular operation by pressing the touch screen in the region of the appropriate icon using at the appropriate time during the surgical procedure to electronically control the operation of the biopsy device. The present invention is not restricted to use with the particular combination of modes of operation shown in FIG. 15.

For the following description of the modes of operation, it will be assumed for discussion purposes that the first embodiment of the present invention is being described, and that the first switch 146 primarily controls the forward (distal direction) axial movement of the cutter 96, the second switch 148 primarily controls the reverse (proximal direction) axial movement of the cutter 96, and that the third switch 150 primarily controls the fluidic connection of the handpiece 20 to the fluid collection system 22. The switches, 146, 148, and 150, also have secondary functions such as setting the control unit 342 for particular steps during the operation of the instrument, and these secondary functions are described later. The modes of operation are also applicable to the second embodiment of the present invention which includes first switch 276, second switch 278, and third switch 280.

Each mode of operation is utilized for a particular portion of the general biopsy procedure. The "Prime" mode of operation is selected when the operator is preparing the instrument for use. When an operator activates the "Prime" mode of operation by, for example, touching the LCD display 344 in the region of icon 346, the display 334 indicates the status as being "Prime Mode". The cutter 96 then translates to the third position just proximal to the port 78. Once the cutter is in the third position, the display instructs the operator to apply saline to the port 78 and to depress the vacuum switch 150 as needed to draw saline into piercer 70 and through the probe assembly 40. The operator may observe the flow of saline through the window 58. Finally, the first pinch valve 314 and second pinch valve 316 are both set to respond to the vacuum switch 150.

The "Insert" mode of operation is next selected when the operator is preparing the instrument for insertion into the tissue of the surgical patient. When an operator activates the "Insert" mode of operation by, for example, touching the LCD display 344 in the region of Icon 348, the display 344 indicates the status as being "Insert Mode". The cutter 96 then translates to the fourth position, just distal to the port 78. Once the cutter 96 translates to the fourth position, the display indicates that the instrument is ready to insert.

The "Verify" mode of operation is selected when the operator wants to verify that the position of the port 78 is adjacent to the tissue to be extracted. In order to more easily visualize the port 78 of the inserted piercer 70 on the imaging device, it has been found that the cutter 96 should be retracted to a position proximal to the port 78, that is, the port 78 should be "open." If the port 78 is not adjacent to the tissue to be extracted, then the operator should "close" the port 78 by moving the cutter 96 to the fourth position, so that the piercer 70 may be hand-manipulated towards the tissue to be extracted. Then the port 78 should be opened again to verify that the port 78 is adjacent to the tissue to be extracted. These steps are repeated until the port 78 is adjacent to the tissue to be extracted. When an operator activates the "Verify" mode of operation by, for example, touching the LCD display 344 in the region of Icon 350, the display 344 indicates the status as being "Verify Mode". If the cutter 96 is not at the fourth position (the port 78 is "open"), the second motor 340 is set to respond to the handpiece first (forward) switch 146. Then the display 344 instructs the operator to close the port 78 by pressing the first (forward) switch 146 on the handpiece 20. When the operator presses the first (forward) switch 146, the cutter 96 translates to the fourth position. The second motor 340 is then set to respond to the handpiece second (reverse) switch 148. If the cutter 96 is already at the fourth position when the "Verify" mode is selected, then the second motor 340 is set to respond to the second (reverse) switch 148. Then the display 344 instructs the operator to open the port 78 by pressing the second (reverse) switch 148 on the handpiece. When the operator presses the second (reverse) switch 148, the cutter 96 translates to the third position just proximal to the port 78. Then the second motor 340 is set to respond to the first (forward) switch 146.

The "Sample" mode of operation is selected when the operator desires to extract a portion of tissue from the surgical patient. When the operator activates the "Sample" mode of operation by, for example, touching the LCD display 344 in the region of icon 352, the display 344 indicates the status as being "Sample Mode". The cutter 96 then translates to the third position which is just proximal to the port 78. Then the second motor 340 is set to respond to the first (forward) switch 146. Once the cutter 96 is in the third position, the display 344 instructs the operator to take a tissue sample by pressing the first (forward) switch 146 on the handpiece. When the first (forward) switch 146 is pressed, the first pinch valve 314 and second pinch valve 316 are opened, and the first motor 338 is activated to rotate the cutter 96 at the appropriate speed. Then the cutter 96 translates to the fourth position, severing the tissue portion prolapsed into the port 78 as the cutter 96 moves distally. Once the cutter 96 reaches the fourth position, the first motor 338 is deactivated and the cutter 96 stops rotating. Then the first pinch valve 314 is activated to close. Next the display 344 instructs an operator to retrieve a tissue sample by pressing the second (reverse) switch 148 on the handpiece 20. The second motor is set to respond to the second (reverse) switch 148 on the handpiece 20. When the operator presses the second (reverse) switch 148, the cutter 96 translates to the first, fully retracted position, just distal to the sampling surface 64. Then the second pinch valve 316 is activated to close the vacuum for the tissue remover 132. A "smart-vacuum" is also activated and a plurality of vacuum pulses (0.5 seconds on and 0.5 seconds off) are supplied to the second vacuum tube 136. A detailed description of the "smart vacuum" is provided in U.S. patent application Ser. No. 08/878,468 filed by the same assignee as for the present application and which is incorporated herein for reference. The display 344 instructs the operator to remove the tissue sample. If there was no sample extracted, that is, the severed tissue portion remained at the distal end of the piercer 70 rather than be deposited onto the tissue sample surface 64, the operator is instructed to select "Dry Tap". The operator is also instructed to select "Remove Air/Blood" if required to remove excessive fluids in the patient and probe assemble 40. The operator is sally instructed to press the first (forward) switch 146 on the handpiece 20 to extract the next sample. Next, the second motor 340 is set to respond to the first (forward) switch 146 on the handpiece 20. When the first (forward) switch 146 is pressed by the operator, the "smart-vacuum" is stopped and the first and second pinch valves, 314 and 316, are activated to open, and the cutter 96 translates in the distal direction. As the cutter 96 approaches the third position just proximal to the port 78, the first motor 338 is activated to rotate the cutter 96 which then translates to the fourth, fully distal position. Then the cutter 96 rotation is stopped and the first pinch valve 314 is closed to stop the vacuum to the vacuum pressure chamber tube 76 supplied by the first vacuum tube 94.

The "Mark" mode of operation is selected when the operator desires to implant a metallic marker within the surgical patient at the location from which the tissue was extracted. When the operator activates the "Mark" mode of operation by, for example, touching the display 344 in the region of icon 354, the display 344 indicates the status as being "Marker Mode" and also prompts the operator to select "Dry Tap" if required. Then the operator is instructed to press the third (vacuum) switch 150 on the handpiece 20 to activate the "Mark" mode. A marking instrument which may be used in combination with the present invention for marking tissue is commercially available under the tradename MICROMARK from Ethicon Endo-Surgery, Inc., Cincinnati, Ohio. A complete description of the MICROMARK applier and clip, and the method of its use, is included in U.S. patent application Ser. No. 09/105,757 and Ser. No. 09/105,570, both filed on Jun. 26, 1998, and which are incorporated herein for reference. When the operator presses the third (vacuum) switch 150, the cutter 96 translates to the first position just proximal to the tissue sampling surface 64. The display 344 then instructs the operator to insert the MICROMARK instrument, to press the third (vacuum) switch 150 on handpiece when ready to deploy, and to deploy the marker. Then when the third (vacuum) switch 150 is pressed, the first pinch valve 314 is activated to the open position for five seconds to supply vacuum to the port 78 through the vacuum chamber 76. Next the display 344 instructs the operator to reposition the MICROMARK instrument if marker deployment was not complete, to press the third (vacuum) switch 150 on the handpiece when ready to deploy the marker, to deploy the marker, and if the marker deployment is complete, to remove the MICROMARK instrument.

The "Remove" mode of operation is selected when the operator is ready to remove the piercer 70 from within the tissue of the surgical patient. When the operator activates the "Remove" mode of operation by, for example, touching the display 344 in the region of icon 356, the display 344 indicates the status as being "Remove Mode". The cutter 96 translates to the fourth, fully distal position and closes the port 78. The display 344 instructs the operator that the instrument is ready to remove.

The "Remove Air/Blood" mode of operation is selected when the operator desires to remove any fluids present near the distal end of the piercer 78 and within the probe assembly 40. When the operator activates the "Remove Air/Blood" mode of operation by, for example, pressing the display 344 in the region of icon 360, the display 344 indicates the status as being "Remove Air/Blood Mode". The cutter 96 then translates to the third position just proximal to the port 78. The first pinch valve 314 and the second pinch valve 316 are both set to respond to the third (vacuum) switch 150 on the handpiece 20. The display then instructs the operator to remove the air/blood by pressing the third (vacuum) switch 150 on the handpiece 20. When the third (vacuum) switch 150 is pressed, the first pinch valve 314 and the second pinch valve 316 are activated to open for five seconds. When they are closed, the cutter 96 then translates to the first, fully retracted position just proximal to the tissue sampling surface 64. Then the "Remove Air/Blood" mode is automatically exited and the previous mode selected is automatically reset.

The "Dry Tap" mode of operation is selected when the operator had attempted to extract a tissue portion from the surgical patient using the "Sample" mode of operation, but a tissue portion was not deposited onto the tissue sample surface 64. This may occur when the tissue portion is properly severed from the surgical patient, but remained in the distal end of the piercer 78. When the operator activates the "Dry Tap" mode of operation by, for example, touching the display 344 in the region of icon 358, the display 344 indicates the status as being "Dry Tap Mode". The cutter 96 then translates to the third position just proximal to the port 78. Then the second pinch valve 316 is activated to open for 0.5 seconds and to close for 0.5 seconds three times in order to pulse the vacuum supplied to the tissue remover 132 through the second vacuum tube 136. The cutter 96 then translates to the first, fully retracted position just proximal to the tissue sampling surface 64. The "Dry Tap" mode of operation is then exited and the previously selected mode of operation is automatically selected.

The "Flush" mode of operation is selected when the operator desires to clear any obstructions (tissue fragments, etc.) on the distal end of the tissue remover 132 to enable the passage of fluids through it. When an operator activates the "Flush" mode of operation by, for example, touching the display 344 in the region of icon 362, the display 344 indicates the status as being "Flush Mode". The cutter 96 then translates to the first, fully retracted position, thus exposing the distal end of the tissue remover 132. Then the control unit 342 is set to respond to the vacuum switch 150, which when pressed by the operator, causes the "Flush" mode of operation to be exited and the previously selected mode of operation to be automatically reset. Before pressing the vacuum switch 150, however, the operator may temporarily disconnect the second connector 304, inject fluid such as saline into the second vacuum tube 136 using a syringe, and reconnect the second connector 304.

The "Inject" mode of operation is selected when the operator desires to inject a fluid, such as a local anesthetic, into the tissue surrounding the distal end of the piercer 78. When the operator activates the "Inject" mode of operation by, for example, touching the display 344 in the region of icon 364, the display 344 indicates the status as being "Inject Mode". The cutter 96 then translates to the third position just proximal to the port 78. Then the control unit 342 is set to respond to the third (vacuum) switch 150 on the handpiece 20. Next the display instructs the operator to inject the fluid into the second vacuum tube 136, and to press the third (vacuum) switch 150 again once the injection is complete. When the operator has completed the injection into the second vacuum tube 136, reconnected it to the fluid collection system 22, and pressed the third (vacuum) switch 150, the cutter 96 translates to the first, fully retracted position. At that point, the "Inject" mode of operation is exited, and the previously selected mode of operation is automatically reset.

Each time one of the available operating modes is selected, a display area 344 provides written and graphic information to prompt the user as to the correct usage of the instrument and the next operational steps. A mode indicator display 370 includes a representation of the probe assembly showing the instantaneous position of the cutter tube, referred to as a cutter position indicator 373, activation of the front vacuum indicator 372 (corresponding with the first vacuum tube 94), and activation of the rear vacuum indicator 371 (corresponding with the second vacuum tube 136).

The present invention, as described, is transportable from room to room of a physician's office, primarily because the handpiece need not be mounted to an X-ray stereotactic table. The remaining portions of the instrument, including the fluid collection system, the power transmission source, and the control unit, may be packaged into a portable, wheeled unit. In one scenario, the physician would have a number of patients, each in a separate room, being prepared for treatment while the surgical procedure is being performed on another patient. The biopsy instrument could then be moved to the patient, rather than vice versa, thus helping the patient to feel relaxed and prepared for the procedure. A different, sterile probe assembly would be provided for each patient, while the holster portion of the handpiece would be reused.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

We claim:
1. A biopsy device, comprising:
 (a) a body;
 (b) a needle extending distally from the body;
 (c) a cutter movable relative to the needle configured to sever tissue;
 (d) a control unit connected to the body;
 (e) a display connected to the control unit, wherein the display includes one or more icons, wherein each icon is representative of at least one operational mode of a plurality of operational modes of the biopsy device, wherein each operational mode of the plurality of operational modes includes a predetermined sequence that is performed by the control unit: and
 (f) at least one user input operable to control at least one operational mode of the biopsy device, wherein the at least one user input is operable to perform a secondary function of setting the control unit for particular steps during the operation of the biopsy device.

2. The biopsy device of claim 1, wherein at least one of the plurality of operational modes includes a first predetermined sequence that is executed by the control unit, wherein the control unit is operable to retract the cutter proximally relative to the needle when the first predetermined sequence is executed.

3. The biopsy device of claim 2, wherein control unit is further operable to apply a vacuum to the biopsy device after receiving a predetermined user input when the first predetermined sequence is executed.

4. The biopsy device of claim 3, wherein the first predetermined sequence corresponds to a user using a marker delivery device in conjunction with the biopsy device.

5. The biopsy device of claim 1, wherein the at least one user input is disposed on the outer surface of the body.

6. The biopsy device of claim 5, further comprising a fluid collection system, wherein the at least one user input is operable to operate the fluid collection system.

7. The biopsy device of claim 5, wherein at least one of the plurality of operational modes corresponds to the biopsy device transitioning to an aspiration state, wherein the control unit is configured to transition the biopsy device to the aspiration state when the at least one user input is actuated by a user.

8. The biopsy device of claim 7, wherein the control unit is configured to apply a vacuum to the needle and the cutter while the biopsy device is in the aspiration state.

9. The biopsy device of claim 7, wherein the control unit is configured to retract the cutter proximally relative to the needle before the biopsy device transitions to the aspiration state.

10. The biopsy device of claim 1, wherein at least one of the plurality of operational modes corresponds to the control unit executing a second predetermined sequence, wherein the control unit is operable to retract the cutter relative to the needle when the second predetermined sequence is executed by the control unit.

11. The biopsy device of claim 10, wherein the control unit is further operable to apply a pulsed vacuum to the cutter when the second predetermined sequence is executed by the control unit.

12. The biopsy device of claim 1, wherein the display is a touch screen, wherein a particular operational mode of the biopsy device is selected by an operator touching one of the icons of the display.

13. The biopsy device of claim 1, wherein each operational mode of the biopsy device corresponds to a particular portion of a biopsy procedure.

14. The biopsy device of claim 1, wherein the cutter is disposed within the needle.

15. The biopsy device of claim 1, wherein the needle includes a lateral tissue receiving feature, wherein the cutter is configured to sever tissue received in the lateral tissue receiving feature.

16. The biopsy device of claim 1, wherein the at least one operational mode of the biopsy device corresponds to a prime mode, wherein the initiation mode includes a predetermined sequence executed by the control unit to prepare at least a portion of the biopsy device for a biopsy procedure.

17. The biopsy device of claim 1, wherein the at least one operational mode of the biopsy device corresponds to a fluid injection mode, wherein the fluid injection mode includes a predetermined sequence executed by the control unit to permit injection of fluid at a biopsy site.

18. A biopsy device, comprising:
(a) a body;
(b) a needle extending distally from the body along a needle axis;
(c) a cutter movable relative to the needle configured to sever tissue;
(d) a control unit connected to the body; and
(e) a display in communication with the control unit, wherein the display is operable to present a plurality of icons to a user, wherein one or more of the plurality of icons are representative of at least one operational mode of a plurality of operational modes of the biopsy device, wherein the control unit is operable to execute each operational mode of the plurality of operational modes,
wherein the plurality of operational modes includes a first operational mode and a
second operational mode, wherein the second operational mode corresponds to a user operating the biopsy device to aspirate a biopsy site when the second operational mode is executed by the control unit.

19. The biopsy device of claim 18, wherein the first operational mode is configured to permit the user to use the biopsy device in conjunction with a marker delivery device when the first operational mode is executed by the control unit.

20. The biopsy device of claim 18, wherein the first operational mode corresponds to a sample mode, wherein the plurality of operational modes further includes a third operational mode and a fourth operational mode, wherein the third operational mode corresponds to a prime mode, wherein the fourth operational mode corresponds to a flush mode.

21. A biopsy device comprising:
(a) a probe assembly, wherein the probe assembly comprises:
(i) an elongate piercer, the piercer having a piercer lumen, a closed, sharpened distal end configured to pierce tissue, and a port proximal to the sharpened distal end configured to receive a portion of a tissue mass, and
(ii) an elongate cutter having a distal end, a proximal end, and a cutter lumen therethrough, the cutter being disposed coaxially and slidably relative to the piercer, wherein the cutter distal end is configured to cut a portion of tissue protruding into the port of the piercer when the cutter moves distally past the port;
(b) a cutter drive assembly, wherein the cutter drive is operable to drive the cutter;
(c) a control unit, wherein the control unit includes a display, wherein the cutter drive is in communication with the control unit, wherein the control unit is operable to receive user inputs from the display, wherein the cutter drive assembly is at least partially responsive to the control unit in response to a user selecting a plurality of icons presented on the display, wherein the control unit is operable to execute an operational mode of a plurality of operational modes in response to a user selecting at least one of the plurality of icons presented on the display; and
(d) at least one user input remote from the control unit, wherein at least one of the plurality of modes corresponds to the biopsy device transitioning to an aspiration state, wherein the control unit is configured to transition at least a portion of the biopsy device to the aspiration state when the at least one user input is actuated by a user.

22. The biopsy device of claim 21, wherein the at least one of the plurality of modes corresponds to a prime mode, wherein the control unit is configured to execute a predetermined sequence to prepare the probe assembly for a biopsy procedure.

23. The biopsy device of claim 21, wherein at least one of the plurality of modes corresponds to a sample mode, wherein the control unit is configured to execute a predetermined sequence to actuate the cutter of the probe assembly and acquire one or more tissue samples.

24. The biopsy device of claim 21, wherein the at least one of the plurality of modes corresponds to a prime mode, wherein at least one of the plurality of modes corresponds to a sample mode, wherein at least one of the plurality of modes corresponds to a flush mode.

* * * * *